(12) United States Patent
MacDonald et al.

(10) Patent No.: US 9,322,114 B2
(45) Date of Patent: Apr. 26, 2016

(54) POLYPROPYLENE FIBERS AND FABRICS

(71) Applicants: ExxonMobil Chemical Patents Inc., Baytown, TX (US); Reifenhäuser GmbH & Co. KG Maschinenfabrik, Troisdorf (DE)

(72) Inventors: Jeanne Marie MacDonald, Sugar Land, TX (US); Antonios K. Doufas, Baytown, TX (US); Jerome Sarrazin, Sint Stevens Woluwe (BE); William Michael Ferry, Houston, TX (US); Rahul Ravindra Kulkarni, Houston, TX (US); Derek Wade Thurman, Houston, TX (US); Cynthia Ann Mitchell, Houston, TX (US); Detlef Frey, Niederkassl (DE); Peter Schlag, Troisdorf (DE); Hans-Georg Geus, Niederkassel (DE); Claudio Cinquemani, Köln (DE)

(73) Assignees: EXXONMOBIL CHEMICAL PATENTS INC., Baytown, TX (US); REIFENHAUSER GMBH & CO. KG MASCHINENFABRIK, Troisdorf (DE)

( * ) Notice: Subject to any disclaimer, the term of this patent is extended or adjusted under 35 U.S.C. 154(b) by 593 days.

(21) Appl. No.: 13/691,984

(22) Filed: Dec. 3, 2012

(65) Prior Publication Data

US 2014/0155854 A1    Jun. 5, 2014

(51) Int. Cl.
*D04H 1/00* (2006.01)
*D04H 3/00* (2012.01)
(Continued)

(52) U.S. Cl.
CPC . *D01F 6/06* (2013.01); *A61F 13/53* (2013.01); *D04H 1/435* (2013.01); *D04H 3/14* (2013.01);
(Continued)

(58) Field of Classification Search
None
See application file for complete search history.

(56) References Cited

U.S. PATENT DOCUMENTS

| 3,849,241 A | 11/1974 | Butin et al. |
| 3,973,068 A | 8/1976 | Weber |

(Continued)

FOREIGN PATENT DOCUMENTS

| EP | 1 023 471 | 8/2000 |
| EP | 1 340 843 A1 | 9/2003 |

(Continued)

OTHER PUBLICATIONS

PCT International Search Report dated Mar. 14, 2014, which issued in corresponding International Application No. PCT/EP2013/074655, filed Nov. 25, 2013 (9 pgs).

(Continued)

*Primary Examiner* — Angela Ortiz
*Assistant Examiner* — Klee S Simmons
(74) *Attorney, Agent, or Firm* — Nixon & Vanderhye P.C.

(57) ABSTRACT

This invention relates to polypropylene fibers and fabrics containing polypropylene fibers, the fibers comprising propylene polymers comprising at least 50 mol % propylene, said polymers having: a) a melt flow rate (MFR, ASTM 1238, 230° C., 2.16 kg) of about 10 dg/min to about 25 dg/min; b) a dimensionless Stress Ratio/Loss Tangent Index $R_2$ [defined by Eq. (8)] at 190° C. from about 1.5 to about 30; c) an onset temperature of crystallization under flow, $T_{c,rheol}$, (as determined by SAOS rheology, 190° C., 1° C./min, where said polymer has 0 wt % nucleating agent present), of at least about 123° C.; d) an average meso run length determined by $^{13}$C NMR of at least about 55 or higher; and e) optionally, a loss tangent, tan δ, [defined by Eq. (2)] at an angular frequency of 0.1 rad/s at 190° C. from about 14 to about 70.

32 Claims, 2 Drawing Sheets

(51) Int. Cl.
  D04H 5/00    (2012.01)
  D04H 13/00   (2006.01)
  D01F 6/06    (2006.01)
  A61F 13/53   (2006.01)
  D04H 1/435   (2012.01)
  D04H 3/14    (2012.01)
  C08L 23/10   (2006.01)

(52) U.S. Cl.
  CPC ............ C08L 23/10 (2013.01); C08L 2203/12
      (2013.01); Y10T 428/2904 (2015.01); Y10T
      428/298 (2015.01); Y10T 442/60 (2015.04);
         Y10T 442/608 (2015.04); Y10T 442/66
      (2015.04); Y10T 442/671 (2015.04); Y10T
      442/68 (2015.04); Y10T 442/681 (2015.04);
                      Y10T 442/696 (2015.04)

(56) References Cited

U.S. PATENT DOCUMENTS

| | | |
|---|---|---|
| 4,070,218 A | 1/1978 | Weber |
| 4,112,159 A | 9/1978 | Pall |
| 4,526,733 A | 7/1985 | Lau |
| 4,578,414 A | 3/1986 | Sawyer et al. |
| 4,855,360 A | 8/1989 | Duchesne et al. |
| 4,863,983 A | 9/1989 | Johnson et al. |
| 4,923,914 A | 5/1990 | Nohr et al. |
| 4,940,464 A | 7/1990 | Van Gompel et al. |
| 5,025,052 A | 6/1991 | Crater et al. |
| 5,075,068 A | 12/1991 | Milligan et al. |
| 5,080,569 A | 1/1992 | Gubernick et al. |
| 5,145,727 A | 9/1992 | Potts et al. |
| 5,160,746 A | 11/1992 | Dodge, II et al. |
| 5,272,003 A | 12/1993 | Peacock |
| 5,459,188 A | 10/1995 | Sargent et al. |
| 5,607,701 A | 3/1997 | Allen et al. |
| 5,696,191 A | 12/1997 | Nohr et al. |
| 5,723,217 A | 3/1998 | Stahl et al. |
| 5,726,103 A | 3/1998 | Stahl et al. |
| 5,766,389 A | 6/1998 | Brandon et al. |
| 5,798,402 A | 8/1998 | Fitzgerald et al. |
| 5,891,814 A | 4/1999 | Richeson et al. |
| 6,143,686 A | 11/2000 | Vizzini et al. |
| 6,218,011 B1 | 4/2001 | Raetzsch et al. |
| 6,416,699 B1 | 7/2002 | Gownder et al. |
| 6,444,774 B1 | 9/2002 | Stahl et al. |
| 6,476,135 B1 | 11/2002 | Bugada et al. |
| 6,537,473 B2 | 3/2003 | Raetzsch et al. |
| 6,583,076 B1 | 6/2003 | Pekrul et al. |
| 6,645,190 B1 | 11/2003 | Olson et al. |
| 6,710,134 B2 | 3/2004 | Demain |
| 6,723,795 B1 | 4/2004 | Dupire et al. |
| 6,747,114 B2 | 6/2004 | Karandinos et al. |
| 7,105,603 B2 | 9/2006 | Dharmarajan et al. |
| 7,319,122 B2 | 1/2008 | Cheng et al. |
| 7,781,527 B2 | 8/2010 | Autran et al. |
| 8,138,107 B2 | 3/2012 | Bornemann et al. |
| 8,247,052 B2 * | 8/2012 | Loyens et al. ............... 428/36.9 |
| 2004/0005457 A1 | 1/2004 | DeLucia et al. |
| 2006/0008643 A1 | 1/2006 | Lin et al. |
| 2006/0241254 A1 | 10/2006 | Razavi |
| 2008/0160862 A1 | 7/2008 | Sartori et al. |
| 2008/0172840 A1 | 7/2008 | Kacker et al. |
| 2008/0182940 A1 | 7/2008 | Dharmarajan et al. |
| 2009/0022956 A1 | 1/2009 | Hisamoto |
| 2009/0053959 A1 | 2/2009 | Datta et al. |
| 2009/0098786 A1 | 4/2009 | Tajima et al. |
| 2009/0200647 A1 | 8/2009 | Mondal et al. |
| 2010/0105274 A1 | 4/2010 | Haubruge et al. |
| 2010/0124864 A1 | 5/2010 | Dharmarajan et al. |
| 2010/0233927 A1 | 9/2010 | Standaert et al. |
| 2010/0233928 A1 * | 9/2010 | Ferry et al. ............... 442/401 |
| 2011/0059668 A1 | 3/2011 | Bieser et al. |
| 2011/0081817 A1 | 4/2011 | Bieser et al. |
| 2011/0086568 A1 | 4/2011 | Standaert et al. |
| 2011/0184136 A1 | 7/2011 | Haubruge et al. |
| 2011/0189917 A1 | 8/2011 | Masuda et al. |
| 2011/0207883 A1 * | 8/2011 | Doufas et al. ............... 525/53 |
| 2011/0253152 A1 * | 10/2011 | Lin et al. ............... 128/849 |
| 2012/0116338 A1 | 5/2012 | Ferry et al. |

FOREIGN PATENT DOCUMENTS

| | | |
|---|---|---|
| EP | 1 711 557 | 10/2006 |
| EP | 2 096 197 A1 | 9/2009 |
| EP | 2 126 168 B1 | 2/2011 |
| EP | 2 325 248 B1 | 5/2011 |
| EP | 2 479 331 A1 | 7/2012 |
| JP | 2007-23398 A | 2/2007 |
| WO | WO 99/19547 A1 | 4/1999 |
| WO | WO 00/37009 A2 | 6/2000 |
| WO | WO 01/94462 A1 | 12/2001 |
| WO | WO 2004/005601 A1 | 1/2004 |
| WO | WO 2004/029342 A1 | 4/2004 |
| WO | WO 2005/073309 A1 | 8/2005 |
| WO | WO 2005/111282 A1 | 11/2005 |
| WO | WO 2006/044083 A1 | 4/2006 |
| WO | WO 2006/118794 A2 | 11/2006 |
| WO | WO 2007/024447 A1 | 3/2007 |
| WO | WO 2007/142726 A1 | 12/2007 |
| WO | WO 2009/026207 A1 | 2/2009 |
| WO | WO 2009/103810 A1 | 8/2009 |
| WO | WO 2010/039579 A1 | 4/2010 |
| WO | WO 2010/087921 A1 | 8/2010 |

OTHER PUBLICATIONS

Michielson, et al; "Review of Thermally Point-bonded Nonwovens: Material, Processes and Properties"; *J. App. Pol. Sci.*, 2005, 99, 2489-2496.

Bhat, et al; "Thermal Bonding of Polypropylene Nonwovens: Effect of Bonding Variables on the Structure and Properties of the Fabrics"; *J. App. Pol. Sci.*, 2004, 92, 3593-3600.

Van A. Wente; "Superfine Thermoplastic Fibres", *Ind. Eng. Chem.*, 1956, 48(8), 1342-1346.

Berzin, et al; "Rheological Behavoir of Controlled-Rheology Polypropylenes Obtained by Peroxide-Promoted Degradation During Extrusion: Comparison Between Homopolymer and Copolymer"; *J. of App. Pol. Sci.*, 2001, 80, 1243-1252.

Bond, et al; "Melt Spinning of Metallocene Catalyzed Polypropylenes, I. On-Line Measurements and Their Interpretation"; *J. App. Pol. Sci.*, 2001, 82, 3223-3236.

Lu, et al; "The Influence of Resin Characteristics on the High Speed Melt Spinning of Isotactic Polypropylene. I. Effect of Molecular Weight and Its Distribution on Structure and Mechanical Properties of As-Spun Filaments", *J. App. Pol. Sci.*, 1987, 34, 1521-1539.

Lu, et al; "The Influence of Resin Characteristics on the High Speed Melt Spinning of Isotactic Polypropylene. II. On-Line Studies of Diameter, Birefringence, and Temperature Profiles"; *J. App. Pol. Sci.*, 1987, 34, 1541-1556.

Lu, et al; "The Role of Crystallization Kinetics in the Development of the Structure and Properties of Polypropylene Filaments", *J. App. Pol. Sci.*, 1993, 49, 623-631.

Lumicene® MR 2001 and MR 2002 a step forward for nonwovens, Polypropylene, Total Petrochemicals, Oct. 2010 (2 pgs).

Spruiell et al; "The Influence of Isotacticity, Ethylene Comonomer Content, and Nucleating Agent Additions on the Structure and Properties of Melt-Spun Isotactic Polypropylene Filaments", *Journal of Applied Polymer Science*, 1996, vol. 62, pp. 1965-1975.

Standard Test: WSP 110.4(05), Standard Test Method for Breaking Force and Elongation of Nonwoven Materials (Strip Method) This (04) Version Includes Both INDA $1^{st}$ 110.4 (02) (Option A) and EDANA ERT 20.2-89 (Option B), Reference No. WSP 110.4 (05) A, 2005, pp. 11.11-11.20.

Polypropylene HF420FB Polypropylene Homopolymer, Sep. 24, 2010, Ed. 4, pp. 1-2.

ExxonMobil Chemical Achieve™ 3854 Polypropylene Homopolymer, Mar. 23, 2012, pp. 1-2.

(56) References Cited

OTHER PUBLICATIONS

ExxonMobil Chemical ExxonMobil™ PP3155 Polypropylene Homopolymer, Mar. 23, 2012, pp. 1-2.

Product Data and Technical Information, Product Name: Moplen, Grade: PP567P, Copyright 2008 Basell Service Company B.V., Mar. 23, 2012 (1 pg).

Product Data and Technical Information, Product Name: Moplen, Grade: HP552N, Copyright 2008 Basell Service Company B.V., Mar. 23, 2012 (1 pg).

Total Petrochemicals Polypropylene Lumicene® MR 2002, Technical Data Sheet, Feb. 2010, pp. 1-2.

Total Petrochemicals, "Lighter Spunbond Nonwoven Fabrics with Lumicene® MR 2001 and MR2002 Polypropylene"; Technical Data Sheet, Oct. 2011 (2 pgs).

"At Home in Your World, Polypropylene European Product Range for Fibre Applications"; Total Petrochemicals, Oct. 2010, pp. 1-7.

"Polypropylene Homopolymers (PPH)", Total Petrochemicals, Apr. 2012 (1 pg).

PCT Notification Concerning Transmittal of International Preliminary Report on Patentability; PCT International Preliminary Report on Patentability; and PCT Written Opinion of the International Searching Authority, mailed Jun. 18, 2015; Int'l Application No. PCT/EP2013/074655; Int'l Filing Date Nov. 25, 2013 (6 pgs.).

* cited by examiner

POLYPROPYLENE FIBERS AND FABRICS

STATEMENT OF RELATED CASES

This application relates to concurrently filed U.S. patent application Ser. No. 61/732,451 entitled "Propylene Polymers" assigned to ExxonMobil Chemical Patents Inc.

FIELD OF THE INVENTION

This invention relates to fibers made from propylene polymers, yarns and fabrics made from the fibers, and articles made from the fibers, yarns and fabrics. The fibers and fabrics have an excellent combination of tensile and textural properties useful in various applications, such as hygiene products, medical products and consumer products.

BACKGROUND OF THE INVENTION

Polypropylene is conventionally used to produce fibers and spunbond nonwovens for a wide range of articles, such as, for example, disposable hygiene goods including diapers, sanitary napkins, training pants, adult incontinence products, hospital gowns, baby wipes, moist towelettes, cleaner cloths, and the like. The typical polypropylene nonwoven fabric can mimic the appearance, texture and strength of a woven fabric. In combination with other materials they provide a spectrum of products with diverse properties, and are also used alone or as components of apparel, home furnishings, health care, engineering, industrial and consumer goods. Conventionally, propylene based materials such as polypropylene that present excellent spinnability (e.g. stable fabrication without breaks of thin fibers on the order of about 0.7-2 denier and particularly about 1-1.5 denier) suffer from poor fiber and/or fabric properties (e.g. low tensile strength/tenacity). Inversely, polypropylene compositions that exhibit acceptable fiber/fabric properties such as good tensile strength have poor processability associated with fiber breaks and drips in the spinline, particularly when thin fibers are made (e.g. <20 microns or equivalently <2 denier). Thus, there is a general interest to impart superior tensile strength in both machine direction (MD) and transverse direction (TD, also referred to as Cross Direction, CD) of polypropylene nonwoven fabrics, while exhibiting excellent processability and spinnability, particularly for applications requiring improved mechanical strength such as disposable hygiene articles.

Likewise, in general, at low fabric basis weights (e.g. <15 g/m$^2$), high line speeds (e.g. >600 m/min) and high throughput rates, conventional polypropylene resins do not provide the desired fabric strength properties. Thus, it is desirable to develop polypropylene fibers and fabrics that exhibit high fabric strength at low fabric basis weights and high line speeds. This allows the fabric converter to downgauge the spunbonding process utilizing less polypropylene resin (lower basis weight fabric) without sacrificing fabric mechanical properties. When used to prepare low basis weight (less than about 15 g/m$^2$) spunbond fabrics at high line speeds (such as 900 m/min or more), typical polypropylene resins tend to show specific tensile strengths (tensile strength in N per 5 cm fabric width divided by fabric basis weight) of roughly 1 N/5 cm/gsm or less (where gsm is g/m$^2$) in the transverse(cross) direction when run in a three beam spunbonding configuration.

Additional references of interest include: U.S. Pat. Nos. 7,105,603; 6,583,076; 5,723,217; 5,726,103; U.S. Patent Publication Nos. 2010/233927; 2011/059668; 2011/081817; 2012/0116338, 2010/0233928; 2008/0182940; 2008/0172840; 2009/0022956; PCT Publication Nos. WO 2010/087921; WO 2006/044083; WO 2006/118794; WO 2007/024447; WO 2005/111282; WO 2001/94462; JP 2007-023398 A (JAPAN POLYCHEM CORP, Feb. 1, 2007); and Journal Of Applied Polymer Science, John Wiley and Sons Inc., New York, May 2001, Vol. 80, No. 8, pp. 1243-1252. US2012-0116338A discloses spunbond fibers made from visbroken polypropylene with a melt flow rate of greater than 50 dg/min. US2010/0233928A discloses fabrics comprising fine meltspun fibers comprising one or more primary polypropylenes having a molecular weight distribution of less than 3.5 and a melt flow rate within the range from 5 to 500 dg/min, the fibers having at least one of an average diameter of less than 20 μm or a denier (g/9000 m) of less than 2.0.

BRIEF SUMMARY OF THE INVENTION

This invention relates to fibers that have an excellent combination of properties, including fiber strength/tenacity, and to nonwoven fabrics comprising the fibers, the fabrics having advantageous tensile properties and textural properties even at low fabric basis weight strengths and/or when produced at high production line speeds. The fibers may be made from propylene polymer compositions having an excellent combination of rheological, crystallization and tacticity properties. Certain advantageous nonwoven fabrics of this invention comprise propylene polymer fibers composed of a propylene polymer comprising at least 50 mol % propylene, said polymer having:

a) a melt flow rate (MFR, ASTM 1238, 230° C., 2.16 kg) of about 10 dg/min to about 21.5 dg/min;

b) a dimensionless Stress Ratio/Loss Tangent Index $R_2$ [defined by Eq. (8) below] at 190° C. from about 1.5 to about 28;

c) an onset temperature of crystallization under flow, $T_{c,rheol}$, (as determined by SAOS rheology, 1° C./min as described below, where said polymer has 0 wt % nucleating agent present), of at least about 131° C.; and d) an average meso run length determined by $^{13}$C NMR of at least about 97 or higher.

The invention also provides a nonwoven fabric having a fabric basis weight of not more than 15 gsm and comprising polypropylene fibers having a dpf value of 0.3 to 5 dpf, wherein said polypropylene fibers comprise a propylene polymer composition comprising at least 50 mol % propylene, said polymer composition having:

a) a melt flow rate (MFR, ASTM 1238, 230° C., 2.16 kg) of about 10 to 25 dg/min b) a dimensionless Stress Ratio/Loss Tangent Index $R_2$ [defined by Eq. (8)] at 190° C. from 1.5 to 30 c) an onset temperature of crystallization under flow, $T_{c,rheol}$, (as determined by SAOS rheology, 1° C./min as described below, where said polymer has 0 wt % nucleating agent present), of at least about 123° C. and d) an average meso run length determined by $^{13}$C NMR of at least about 55 or higher.

Advantageously, said fabric is obtainable by spunbonding with a production line speed of at least 400 m/min and/or has a fabric tensile anisotropy as defined herein of less than 3.0 when produced at a production line speed of 900 m/min.

Furthermore the invention provides a nonwoven fabric having a fabric basis weight of not more than 15 gsm and comprising polypropylene fibers having a dpf value of 0.3 to 5 dpf, wherein: said nonwoven fabric is obtainable by spunbonding with a production line speed of at least 400 m/min; said polypropylene fibers comprise a propylene polymer of filaments and yarns. Many yarns consist of a multiplicity of filaments.

a) a melt flow rate (MFR, ASTM 1238, 230° C., 2.16 kg) of about 10 dg/min to about 40 dg/min;
b) a dimensionless Stress Ratio/Loss Tangent Index $R_2$ [defined by Eq. (8) herein] at 190° C. from about 0.6 to about 30;
c) an onset temperature of crystallization under flow, $T_{c,rheol}$, (as determined by SAOS rheology, 1° C./min as described herein, where said polymer has 0 wt % nucleating agent present), of at least about 120° C.; and
d) an average meso run length determined by $^{13}C$ NMR of at least about 65 or higher; and said fabric has a ratio of CD elongation to CD peak Strength of 40 or more (when measured at speed of 200 mm/min) and a CD strength of 1.0 N/5 cm/gsm or more.

Moreover the invention provides a polypropylene fiber comprising a propylene polymer comprising at least 50 mol % propylene, said polymer having:
a) a melt flow rate (MFR, ASTM 1238, 230° C., 2.16 kg) of about 10 dg/min to about 21.5 dg/min;
b) a dimensionless Stress Ratio/Loss Tangent Index $R_2$ [defined by Eq. (8) herein] at 190° C. from about 1.5 to about 28;
c) an onset temperature of crystallization under flow, $T_{c,rheol}$, (as determined by SAOS rheology, 1° C./min as described herein, where said polymer has 0 wt % nucleating agent present), of at least about 131° C.; and
d) an average meso run length determined by $^{13}C$ NMR of at least about 97 or higher.

A number of other combinations of rheological, crystallization and tacticity attributes defining the compositions of propylene polymers used in certain illustrative embodiments of the invention are also disclosed herein.

In one exemplary embodiment, fibers and fabrics of the invention may be made from a composition that is a reactor grade propylene polymer or a controlled rheology (visbroken) propylene polymer The propylene polymers may be visbroken propylene polymers, which may be obtainable by a process comprising contacting a propylene polymer having an MFR of 0.1 to 8 dg/min (preferably 0.5 to 6 dg/min, preferably 0.8 to 3 dg/min), with a visbreaking agent (such as peroxide), under conditions sufficient to obtain a propylene polymer having a) an MFR of 10 dg/min or more, preferably from 10 to 25, preferably from 14 to 19 dg/min as further described herein.

Fibers of this invention have excellent tensile properties, for example tensile strength, elongation and flexural modulus. Fabrics made from the fibers have excellent combinations of tensile properties and textural properties, for example hand. This invention also relates to spunbonded nonwoven fabrics having the desirable combination of high fabric strength (both in MD and CD directions) at low fabric basis weights (e.g. less than 15 gsm) and high fabric production line speeds (e.g. greater than 400 m/min, especially greater than 600 m/min) The fibers and fabrics of this invention can be manufactured at high line speeds with excellent processability/spinnability.

DEFINITIONS

Figure 1:
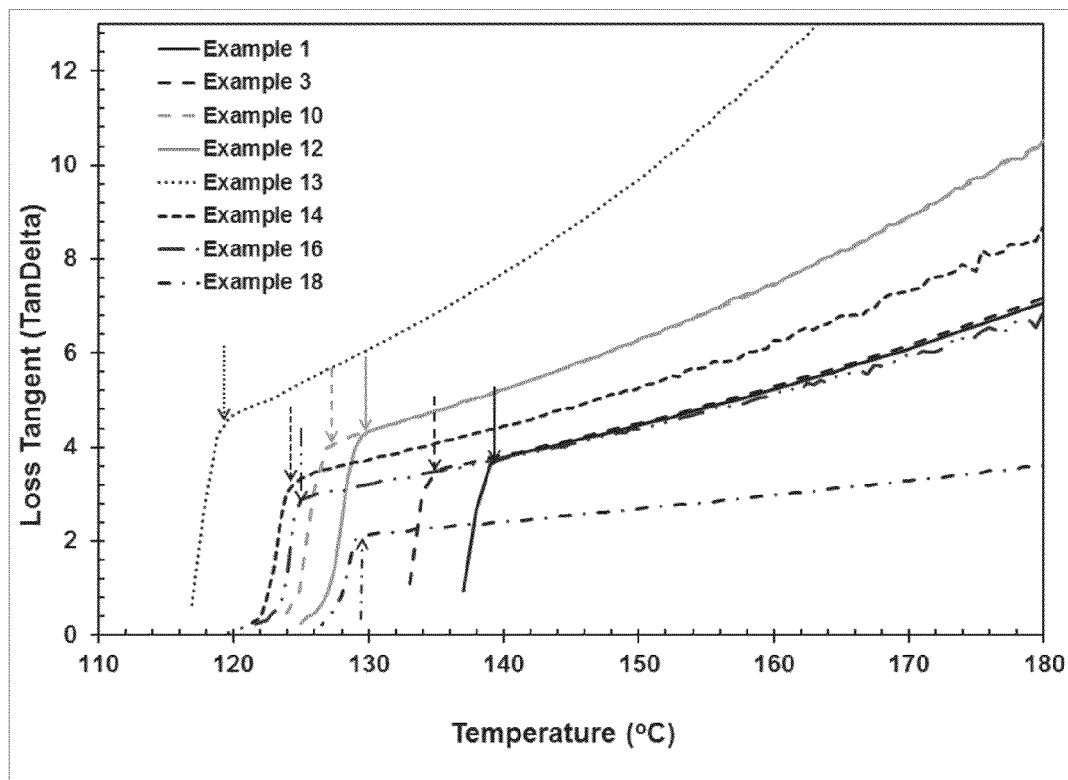
FIG. 1 depicts the evolution of the loss tangent (tan δ) under a cooling SAOS rheological experiment.

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, including, but not limited to ethylene, propylene, and butene, the olefin present in such polymer or copolymer is the polymerized form of the olefin. For example, when a copolymer is said to have a "propylene" content of 35-55 wt %, it is understood that the mer unit in the copolymer is derived from propylene in the polymerization reaction and said derived units are present at 35-55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. The term "different" as used to refer to mer units indicates that the mer units differ from each other by at least one atom or are different isomerically. Accordingly, the definition of copolymer, as used herein, includes terpolymers and the like. A "propylene polymer," also referred to as "polypropylene," is a polymer comprising 50 mol % or more units derived from propylene. An oligomer is typically a polymer having a low molecular weight (such an Mn of less than 25,000 g/mol, preferably less than 2,500 g/mol) or a low number of mer units (such as 75 mer units or less).

As used herein, the new notation for the Periodic Table Groups is used as described in *Chemical and Engineering News*, 63(5), 27 (1985).

As used herein, "metallocene catalyst" means a Group 4 transition metal compound having at least one cyclopentadienyl, indenyl or fluorenyl group attached thereto that is capable of initiating olefin catalysis, typically in combination with an activator.

The terms "catalyst" and "catalyst compound" are defined to mean a compound capable of initiating catalysis. In the description herein, the catalyst may be described as a catalyst precursor, a pre-catalyst compound, or a transition metal compound, and these terms are used interchangeably. A catalyst compound may be used by itself to initiate catalysis or may be used in combination with an activator to initiate catalysis. When the catalyst compound is combined with an activator to initiate catalysis, the catalyst compound is often referred to as a pre-catalyst or catalyst precursor. A "catalyst system" is a combination of at least one catalyst compound, an optional activator, an optional co-activator, and an optional support material, where the system can polymerize monomers to polymer. For the purposes of this invention and the claims thereto, when catalyst systems are described as comprising neutral stable forms of the components, it is well understood by one of ordinary skill in the art, that the ionic form of the component is the form that reacts with the monomers to produce polymers.

As used herein, "fibers" may refer to filaments, yarns, or staple fibers.

A "filament" refers to a monolithic fiber also referred to as a "monofilament" or a "continuous filament". For the avoidance of doubt, the term "filament" extends to filaments which are formed and laid down as a fabric in a continuous process, for example a as spunbonded nonwoven, without intervening isolation of the filaments.

A yarn is an assembly of two or more fibers which are assembled with or without twist. Said two or more fibers may be the same or different, but are preferably the same. Fibers used to form a yarn may each independently be a filament, may each independently itself be a yarn, or may be a mixture A "filament yarn" (also referred to herein as a "continuous filament yarn") is an assembly of at least two filaments which are assembled with or without twist.

"Staple fibers" (also referred to herein as "staple") are lengths of filament or yarn which have been cut from continuous filament or yarn. Staple fibers will normally have a uniform length. Typical staple fiber lengths are for example up to 500 mm, especially up to 200 mm, for example a length in the range of from 3 mm to 200 mm.

"Bulked" or "textured" fibers are fibers which have been treated, for example by crimping or other means, to modify texture in a fabric made from the fibers.

In relation to fibers, "partially oriented" refers to spun fibers, especially meltspun fibers, which have been drawn in the melt state without solid state drawing, and "fully oriented" refers to fibers which have undergone solid state orientation, for example by solid state drawing. Fibers which are fully oriented may have been, but have not necessarily been, melt-drawn before they are subjected to solid state drawing.

"Partially oriented yarns" are spun fibers (which may be a single filament or an assembly of more than one filament), especially meltspun fibers, that are partially oriented.

"Fully oriented yarns" are spun fibers (which may be a single filament or an assembly of more than one filament), especially meltspun fibers, that are fully oriented.

Good spinnability is defined in this invention as no fiber breaks, drips or hard pieces occurring for a running period of 8 hours at throughput rates in the range of 0.3 to 0.6 ghm (grams per minute per hole) when forming fibers of about 0.8 to about 5 (preferably 0.8 to about 4, preferably 0.8 to about 2.5, preferably from about 1 to about 1.6) denier for fabrics having a basis weight of 5 to 25 g/m² (preferably about 7 to about 20 g/m², preferably about 8 to about 15 g/m², preferably about 9 to about 11 g/m²). Hard pieces are small plastic aggregates that affect the homogeneity of nonwoven fabric negatively.

For purposes of this invention and the claims thereto, when a polymer is described as having 0 wt % nucleating agent present, it means that no external nucleating agents have been added to the polymer. The phrase does not mean that the polymer contains no "internal nucleating agents," i.e. materials that are present in the neat polymer as produced that act as nucleating agents. When a polymer is described as having a certain property with 0 wt % nucleating agent present, it means the test is conducted on polymer that has had no external nucleating agents added to it. For example the phrase "having a $T_{cp}$ (measured by DSC at a cooling rate of 10° C. per minute) with 0% nucleating agent of at least about 123° C. or higher" means that the polymer in question has a $T_{cp}$ of at least about 123° C. or higher when measured on a sample of the polymer where no external nucleating agents have been added to the polymer prior to the DSC test. This phrase is not meant to indicate that nucleating agents may not be added to the polymers as part of the normal production process.

In this specification, "production line speed" means, in relation to a nonwoven fabric, the linear speed of a web or other surface onto which fibers are laid down to form the nonwoven fabric and thus essentially corresponds to the rate of delivery of the nonwoven fabric from the formation section of a nonwoven fabric formation apparatus.

DETAILED DESCRIPTION

The inventors have surprisingly discovered that fibers made from propylene based compositions characterized by a unique combination of specific melt rheological, crystallization and tacticity molecular parameters exhibit a superior combination of spinnability during manufacture and fiber/fabric tensile properties in the fibers per se and in fabrics comprising said fibers. In one embodiment fibers and fabrics are made from compositions having distinct rheological (including melt elasticity) and shear thinning characteristics, differentiated DSC (differential scanning calorimetry) behavior and crystallization under flow kinetics as monitored by rotational rheometry. Contrary to previous polypropylenes, the preferred compositions from which the fibers of the invention are obtainable do not require narrow molecular weight distributions (Mw/Mn) to achieve enhanced spinnability and fiber properties. Therefore, the compositions do not have to be made with metallocene catalysts to obtain narrow Mw/Mn, although use of metallocene catalysts (and narrow Mw/Mn's) is still feasible as long as the composition satisfies the defined range of compositional attributes described herein. Certain especially preferred compositions described herein are those disclosed in co-pending U.S. application Ser. No. 61/732,451 entitled "Propylene Polymers" assigned to ExxonMobil Chemical Patents Inc. filed on the same date as the present application, the entire disclosure of which is incorporated herein by reference. The fibers of the invention are advantageously partially oriented yarns, fully oriented yarns, monofilaments and staple fibers and are particularly useful for formation of spunbonded fabrics, melt blown fabrics, combinations of spunbonded and melt blown fabric structures as well as partially oriented yarns, fully oriented yarns, and staple fibers.

In a preferred embodiment of the invention the fibers and/or fabrics comprise a visbroken propylene polymer, typically obtainable by visbreaking a propylene polymer having an MFR of about 0.1 to about 8 dg/min (preferably 0.6 to 6 dg/min, preferably 0.8 to 3 dg/min) before forming said fibers or fabric.

In a preferred embodiment of the invention, the fibers and fabrics comprise a visbroken (controlled rheology) propylene polymer or a reactor grade propylene polymer (i.e., a propylene polymer that has not been treated to visbreaking) or combinations thereof. In the case of a visbroken propylene composition, the initial polymer before the visbreaking step will be referred to as the "base polymer".

Polymer Compositions

In a preferred embodiment of the invention, the inventive propylene polymer compositions may comprise visbroken (controlled rheology), reactor grade (non visbroken) propylene based polymers and/or combinations thereof. The inventive propylene polymer compositions are preferably formed into fibers, webs, molded parts or other shapes.

In certain preferred embodiments this invention relates to fibers and fabrics comprising propylene polymers comprising at least 50 mol % propylene (preferably at least 80 mol % propylene, preferably at least 90 mol % propylene, preferably 100 mol % propylene), said polymer having:

a) a melt flow rate (MFR, ASTM 1238, 230° C., 2.16 kg) of about 10 to about 21.5 dg/min (preferably 12 to 22 dg/min, preferably 13 to 20 dg/min, preferably 14 to 19 dg/min, preferably 14 to 18 dg/min, preferably 14 to 17 dg/min);

b) a dimensionless Stress Ratio/Loss Tangent Index $R_2$ [defined by Eq. (8) below] at 190° C. from about 1.5 to about 28 (preferably 2 to 15, preferably 2.5 to 6.5);

c) an onset temperature of crystallization under flow, $T_{c,rheol}$, (as determined by SAOS rheology, 1° C./min as described below, where said polymer has 0 wt % nucleating agent present), of at least about 131° C. (preferably 133° C. or more, preferably 135° C. or more, preferably 136° C. or more, preferably 137° C. or more); and d) an average meso run length determined by $^{13}$C NMR of at least about 97 or higher (preferably 97 to 150, preferably 100 to 140, preferably 105 to 130); and optionally e) a loss tangent, tan δ, [defined by Eq. (2) below] at an angular frequency of 0.1 rad/s at 190° C. from about 10 to about 70 (preferably 14 to about 70, preferably 35 to 65, preferably 45 to 55.

In a preferred embodiment of the invention, the propylene polymer is propylene homopolymer.

Preferred inventive propylene polymer compositions useful in fibers and fabrics claimed herein include propylene polymers additionally having one or more of the following properties:

1. an Mw of 30,000 to 2,000,000 g/mol, preferably 150,000 to 300,000, more preferably 190,000 to 240,000, as measured by GPC described in the test methods section; and/or
2. a Tm (second melt, 1° C./min ramp speed, also referred to as "$T_{mp}$") of 100° C. to 200° C., preferably 110° C. to 185° C., preferably 115° C. to 175° C., more preferably 140° C. to 170° C., more preferably 155° C. to 167° C., as measured by the DSC method described below in the test methods; and/or
3. a percent crystallinity (based on the heat of crystallization) of 20% to 80%, preferably 30% to 70%, more preferably 35% to 55% as measured by the DSC method described below in the test methods; and/or
4. a glass transition temperature, Tg, of −50° C. to 120° C., preferably −20° C. to 100° C., more preferably −0° C. to 90° C. as determined by the DSC method described in the test methods; and/or
5. a crystallization temperature, Tc, (1° C./min ramp speed, also referred to as "$T_{cp}$") determined on a sample having 0 wt % nucleating agent of 15° C. to 150° C., preferably 110° C. to 150° C., more preferably 126° C. to 147° C., preferably 129° C. to 139° C., as measured by the DSC method described below in the test methods, and/or
6. a branching index ($g'_{vis}$) of 0.85 or more, preferably 0.90 or more, preferably 0.95 or more, preferably 0.99 or more.

In any embodiment of the invention herein, the inventive fibers or fabrics may comprise propylene polymer compositions having an Mw/Mn of 1 to 7, preferably 1.2 to 5, more preferably 1.5 to 4, as measured by GPC.

In any embodiment of the invention herein, the inventive fibers or fabrics may comprise propylene polymer compositions having an Mz/Mw of 1.5 to 2.5, more preferably 1.8 to 2.2, more preferably 1.9 to 2.1, as measured by GPC.

In any embodiment of the invention herein, the inventive fibers or fabrics may comprise propylene polymer compositions having an onset temperature of crystallization under flow, $T_{c,rheol}$, (determined via SAOS rheology, 1° C./min, 190° C., where the polymer sample to be tested has 0% nucleating agent, as described below) of 131° C. or more, preferably 135° C. or more, preferably 136° C. or more, preferably 137° C.

In any embodiment of the invention herein, the inventive fibers or fabrics may comprise propylene polymer compositions having a Dimensionless Stress Ratio Index $R_1$ [defined by Eq. (7) below] at 190° C. of 1.2 to 4.5, preferably 1.8 to 3.6, preferably 2 to 3, as determined by the SAOS Rheology method described below in the test methods section.

In any embodiment of the invention herein, the inventive fibers or fabrics may comprise propylene polymer compositions having a Dimensionless Stress Ratio/Loss Tangent Index $R_2$ [defined by Eq. (8) below] at 190° C. of about 1.5 to about 28, preferably 2 to 15, preferably 2.5 to 6.5, as determined by the SAOS Rheology method described below in the test methods section.

In any embodiment of the invention herein, the inventive fibers or fabrics may comprise propylene polymer compositions having a Dimensionless Shear Thinning Index $R_3$ [defined by Eq. (9) below] at 190° C. of 6 to 13, preferably 6.5 to 12.5, preferably 7 to 10, as determined by the SAOS Rheology method described below in the test methods section.

In any embodiment of the invention herein, the inventive fibers or fabrics may comprise propylene polymer compositions having a Dimensionless Loss Tangent/Elasticity Index $R_4$ [defined by Eq. (10) below] at 190° C. of 1.5 to 20, preferably 1.7 to 10.7, preferably 2 to 6, as determined by the SAOS Rheology method described below in the test methods section.

In any embodiment of the invention herein, the inventive fibers or fabrics may comprise propylene polymer compositions having a Loss Tangent (tan δ) at an angular frequency of 0.1 rad/s [defined by Eq. (2) below] at 190° C. from about 14 to about 70, preferably 35 to 65, preferably 45 to 55, as determined by the SAOS Rheology method described below in the test methods section.

In any embodiment of the invention herein, the inventive fibers or fabrics may comprise propylene polymer compositions having an average meso run length [defined by Eq. (16) below] of 97 or higher, preferably 100 or higher, preferably 105 or higher, as determined by the $^{13}$C NMR method described below in the test methods section. Alternately, any of the inventive fibers or fabrics may comprise propylene polymer compositions having an average meso run length [defined by Eq. (16) below] of 97 to 150, preferably 100 to 140, preferably 105 to 130. In certain embodiments lower average meso run lengths are possible provided that the average meso run length is at least 55.

In any embodiment of the invention herein, the inventive fibers or fabrics may comprise propylene polymer compositions having a $T_{mp}$ (second heat, measured by DSC at a heating rate of 1° C. per minute) of 120° C. or more, 140° C. or more, preferably 155° C. or more, preferably 160° C. or more, as determined by the DSC method described below in the test methods section.

In any embodiment of the invention herein, the inventive fibers or fabrics may comprise propylene polymer compositions having a $T_{mp}$ (measured by DSC at a heating rate of 10° C. per minute) of 120° C. or more, preferably 140° C. or more, preferably 155° C. or more, preferably 160° C. or more, as determined by the DSC method described below in the test methods section.

In any embodiment of the invention herein, the inventive fibers or fabrics may comprise propylene polymer compositions having a $T_{cp}$ (measured by DSC at a cooling rate of 1° C. per minute, where the polymer to be measured has 0 wt % nucleating agent) of 125° C. or more, preferably 126° C. or more, preferably 127° C. or more, preferably 128° C. or more, preferably 129° C., preferably 130° C. or more, preferably 133° C. or more, as determined by the DSC method described below in the test methods section.

In any embodiment of the invention herein, the inventive fibers or fabrics may comprise propylene polymer compositions having a $T_{cp}$ (measured by DSC at a cooling rate of 10° C. per minute, where the polymer to be tested has 0 wt % nucleating agent) of 115° C. or more, preferably 116° C. or more, preferably 117° C. or more, preferably 118° C. or more, preferably 119° C. or more, preferably 120° C. or more, preferably 121° C. or more, preferably 122° C. or more, preferably 123° C. or more, as determined by the DSC method described below in the test methods section.

In any embodiment of the invention herein, the composition of which the fibers or fabrics are formed may have a supercooling parameter SPC [defined by Eq. (12) below] (measured by DSC at a heating and cooling rate of 1° C. per minute, where the polymer to be tested has 0% nucleating agent) of −11° C. or less, preferably −15° C. or less or preferably less than −17° C., as determined by the DSC method as described below in the test methods section.

In any embodiment of the invention herein, the composition may have a supercooling parameter SPC [defined by Eq. (12) below] (measured by DSC at a heating and cooling rate of 10° C. per minute, where the polymer to be tested has 0% nucleating agent) of about −1° C. or less, preferably −3.5° C. or less, as determined by the DSC method as described below in the test methods section.

In any embodiment of the invention herein, the inventive fibers or fabrics may comprise propylene polymer compositions having an onset temperature of crystallization under flow (determined via SAOS rheology, 1° C./min) $T_{c,rheol}$, where the polymer to be tested has 0 wt % nucleating agent) of 131° C. or more, preferably 135° C. or more, preferably 136° C. or more, preferably 137° C. or more as determined by the SAOS Rheology method described below in the test methods section, and a dimensionless Stress Ratio Index $R_1$ [defined by Eq. (7) below] at 190° C. of 1.2 to 4.5, preferably 1.8 to 3.6, preferably 2-3, as determined by the SAOS Rheology method described below in the test methods section.

In any embodiment of the invention herein, the inventive fibers or fabrics may comprise propylene polymer compositions having a $T_{mp}$ (measured by DSC at a heating of 1° C. per minute) of 140° C. or more, preferably 155° C. or more, preferably 160° C. or more, as determined by the DSC method described below in the Test and Materials section, and dimensionless Stress Ratio Index $R_1$ [defined by Eq. (7) below] at 190° C. of 1.2 to 4.5, preferably 1.8 to 3.6, preferably 2 to 3, as determined by the SAOS Rheology method described below in the test methods section.

In any embodiment of the invention herein, inventive fibers or fabrics may comprise propylene polymer compositions having a $T_{c,rheol}$ of 131° C. or more, preferably 135° C. or more, preferably 136° C. or more, preferably 137° C. or more as determined the SAOS Rheology method described below in the test methods section, and a dimensionless Loss Tangent/Elasticity Index $R_4$ [defined by Eq. (10) below] at 190° C. of 1.5 to 20, preferably 1.7 to 10.7, preferably 2 to 6, as determined by the SAOS Rheology method described below in the test methods section.

In any embodiment herein the inventive fibers or fabrics may comprise propylene polymer compositions having a $T_{cp}$ (measured by DSC at a heating and cooling rate of 1° C. per minute, where the polymer to be tested has 0 wt % nucleating agent) of 125° C. or more (preferably 126° C. or more, preferably 127° C. or more, preferably 128° C. or more, preferably 130° C. or more, preferably 133° C. or more), as determined by the DSC method described below in the Test a section, and a Dimensionless Loss Tangent/Elasticity Index Index $R_4$ [defined by Eq. (10) below] at 190° C. of 1.50 to 20, preferably 1.7 to 10.7, preferably 2 to 6, as determined by the SAOS Rheology method described below in the test methods section.

In any embodiment of the invention herein, the inventive fibers or fabrics may comprise propylene polymer compositions having a $T_{cp}$ (measured by DSC at a cooling rate of 10° C. per minute, where the polymer to be measured has 0 wt % nucleating agent) of 115° C. or more, preferably 116° C. or more, preferably 117° C. or more, preferably 118° C. or more, preferably 119° C. or more, preferably 120° C. or more, preferably 122° C. or more, preferably 123° C. or more, as determined by the DSC method described below in the Test a section, and a dimensionless Loss Tangent/Elasticity Index Index $R_4$ [defined by Eq. (10)] at 190° C. of 1.5 to 20, preferably 1.7 to 10.7, preferably 2 to 6, as determined by the SAOS Rheology method described below in the test methods section.

In any embodiment herein the inventive fibers or fabrics may comprise a propylene polymer composition comprising a propylene based polymer having:
(1) an MFR in the range from about 10 dg/min to about 21.5 dg/min;
(2) a Dimensionless Stress Ratio/Loss Tangent Index $R_2$ [defined by Eq. (8)] at 190° C. from about 1.5 to about 28;
(3) An onset temperature of crystallization under flow $T_{c,rheol}$ (via SAOS rheology, 1° C./min) with 0% nucleating agent of at least about 131° C. or higher;
(4) an average meso run length determined by $^{13}$C NMR of at least about 97 or higher.

In any embodiment herein the inventive fibers or fabrics may comprise a propylene polymer composition comprises a propylene based polymer having:
1) an MFR in the range from about 10 dg/min to about 21.5 dg/min;
2) a Loss Tangent (tan δ) at an angular frequency of 0.1 rad/s [defined by Eq. (2)] at 190° C. from about 14 to about 70;
3) An onset temperature of crystallization under flow $T_{c,rheol}$ (via SAOS rheology, 1° C./min) with 0% nucleating agent of at least about 131° C. or higher;
4) an average meso run length determined by $^{13}$C NMR of at least about 97 or higher.

In any embodiment of the invention herein, the inventive propylene polymer composition comprises a propylene based polymer having:
1) an MFR in the range from about 10 dg/min to about 21.5 dg/min;
2) a Dimensionless Loss Tangent/Elasticity Index $R_4$ (defined by Eq. (10) below) at 190° C. from about 1.5 to about 20;
3) a $T_{cp}$ (measured by DSC at a cooling rate of 1° C. per minute) with 0% nucleating agent of at least about 125° C. or higher; and
4) an average meso run length determined by $^{13}$C NMR of at least about 97 or higher.

In any embodiment of the invention herein, the inventive fibers or fabrics comprise a propylene based polymer having:
1) an MFR in the range from about 10 dg/min to about 21.5 dg/min; and
   a) a Dimensionless Stress Ratio Index $R_1$ (defined by Eq. (7) below) at 190° C. from about 1.2 to about 4.5; or
   b) a Dimensionless Stress Ratio/Loss Tangent Index $R_2$ (defined by Eq. (8) below) at 190° C. from about 1.5 to about 28; or
   c) a Dimensionless Shear Thinning Index $R_3$ (defined by Eq. (9) below) at 190° C. from about 6 to about 13; or
   d) a Dimensionless Loss Tangent/Elasticity Index $R_4$ (defined by Eq. (10) below) at 190° C. from about 1.5 to about 20; or
   e) a Loss Tangent (tan δ) at an angular frequency of 0.1 rad/s (defined by Eq. (2) below) at 190° C. from about 14 to about 70; or
   f) a Stress Ratio (SR) at a shear rate of 500 s$^{-1}$ (defined by Eq. (6) below) at 190° C. from about 3.1 to about 6.1; and
2) a) an onset temperature of crystallization under flow $T_{c,rheol}$ (via SAOS rheology, 1° C./min) with 0% nucleating agent of at least about 131° C. or higher; or
   b) a $T_{cp}$ (measured by DSC at a cooling rate of 1° C. per minute) with 0% nucleating agent of at least about 125° C. or higher; or c) a $T_{cp}$ (measured by DSC at a cooling rate of 10° C. per minute) with 0% nucleating agent of at least about 117° C. or higher; or d) a supercooling parameter SCP (measured by DSC at a heating and cooling rate of 10° C./min) with 0% nucleating agent of less than about −1° C.; or e) a supercooling parameter SCP (measured by DSC at a heating and cooling rate of 1° C./min) with 0% nucleating agent of less than about −11° C.; and 4) a) an average meso run length determined by $^{13}$C NMR of at least about 97 or higher; or b) a total number of defects (stereo and regio) per 10,000 monomers of less than about 103.

In another preferred embodiment of the invention, the inventive fibers or fabrics comprise a propylene polymer composition having:

1) an MFR in the range from about 14 dg/min to about 19 dg/min; and 2) a) a Dimensionless Stress Ratio Index $R_1$ (defined by Eq. (7) below) at 190° C. from about 2.0 to about 3.0; or b) a Dimensionless Stress Ratio/Loss Tangent Index $R_2$ (defined by Eq. (8) below) at 190° C. from about 2.5 to about 6.5; or c) a Dimensionless Shear Thinning Index $R_3$ (defined by Eq. (9) below) at 190° C. from about 7.0 to about 10.0; or d) a Dimensionless Loss Tangent/Elasticity Index $R_4$ (defined by Eq. (10) below) at 190° C. from about 2.0 to about 6.0; or e) a Loss Tangent (tan δ) at an angular frequency of 0.1 rad/s (defined by Eq. (2) below) at 190° C. from about 35 to about 65; or f) a Stress Ratio (SR) at a shear rate of 500 s$^{-1}$ (defined by Eq. (6) below) at 190° C. from about 3.3 to about 4.0; and 3) a) an onset temperature of crystallization under flow $T_{c,rheol}$ (via SAOS rheology, 1° C./min) with 0% nucleating agent of at least about 134° C. or higher; or b) a $T_{cp}$ (measured by DSC at a cooling rate of 1° C. per minute) with 0% nucleating agent of at least about 133° C. or higher; or c) a $T_{cp}$ (measured by DSC at a cooling rate of 10° C. per minute) with 0% nucleating agent of at least about 123° C. or higher; or d) a supercooling parameter SCP (measured by DSC at a heating and cooling rate of 10° C./min) with 0% nucleating agent of less than about −3.5° C.; or e) a supercooling parameter SCP (measured by DSC at a heating and cooling rate of 1° C./min) with 0% nucleating agent of less than about −17.0° C.; and 4) a) an average meso run length determined by $^{13}$C NMR of at least about 100 or higher; or b) a total number of defects (stereo and regio) per 10,000 monomers of less than about 100.

Propylene polymer compositions useful in the inventive fibers or fabrics herein include polypropylene homopolymers, polypropylene copolymers, impact copolymer polypropylenes and blends thereof. The homopolymer may be isotactic polypropylene, syndiotactic polypropylene or blends thereof, including blends with atactic polymer. The copolymer can be a random copolymer, a statistical copolymer, a block copolymer, or blends thereof. The method of making the propylene polymers is not critical, as they can be made by slurry, solution, gas phase, a supercritical polymerization process as the one described in U.S. Pat. No. 7,807,769, a super-solution homogeneous polymerization process as the one described in US Patent Application Publication No. 2010/0113718 or other suitable processes, and by using catalyst systems appropriate for the polymerization of polyolefins, such as Ziegler-Natta-type catalysts, metallocene-type catalysts, other appropriate catalyst systems or combinations thereof. Such catalysts are well known in the art, and are described in, for example, ZIEGLER CATALYSTS (Gerhard Fink, Rolf Mülhaupt and Hans H. Brintzinger, Eds., Springer-Verlag 1995); Resconi et al., *Selectivity in Propene Polymerization with Metallocene Catalysts*, 100 CHEM. REV. 1253-1345 (2000); and I, II METALLOCENE-BASED POLYOLEFINS (Wiley & Sons 2000). In a preferred embodiment useful propylene polymers are made by the catalysts, activators and processes described in U.S. Pat. No. 6,342,566; U.S. Pat. Nos. 6,384, 142; 5,741,563; and PCT Publication Nos. WO 03/04020, and WO 97/19991 US. In another preferred embodiment, the catalysts described in U.S. Pat. No. 7,807,769 and US Patent Application Publication No. 2010/0113718 are useful to make propylene polymers useful herein.

In a preferred embodiment, the propylene polymer compositions of which the inventive fibers or fabrics are composed can be a unimodal reactor grade, a bimodal reactor grade, an in-reactor blend or an extruder blend of two or more propylene polymers (for example a blend of MFR's of 36 dg/min and 2 dg/min). In another embodiment the propylene polymer compositions may have a unimodal, bimodal, or multimodal molecular weight distribution (Mw/Mn) distribution of polymer species as determined by GPC. By bimodal or multimodal is meant that the GPC-SEC trace has more than one peak or inflection point. An inflection point is the point where the second derivative of the curve changes in sign (e.g., from negative to positive or vice versus).

The composition used in the fibers or fabrics of the present invention advantageously presents favorable physical properties of molded parts including high stiffness (flexural modulus), high tensile strength at yield, high yield strain and high heat distortion temperature even without the use of a nucleating agent. In another embodiment, the propylene polymer composition has a 1% secant flexural modulus determined by ASTM D790A (with 0% nucleating agent) of about 190 kpsi or higher, preferably greater than about 200 kpsi, preferably greater than about 210 kpsi.

In another embodiment of the invention, the propylene polymer composition has a yield stress determined by ASTM 638 (with 0% nucleating agent) greater than about 4,700 psi, preferably greater than about 5,000 psi, preferably greater than about 5,100 psi. In another embodiment of the invention, the composition has a yield strain determined by ASTM638 (with 0% nucleating agent) greater than about 7%, preferably greater than about 8% psi and, preferably greater than about 9%.

In another embodiment of the invention, the propylene polymer composition has a tensile strength at yield of about 4,700 psi or higher, preferably greater than about 5,000 psi, preferably greater than about 5,100 psi (as determined by ASTM 638 with 0 wt % nucleating agent).

In another embodiment of the invention, the composition of which the inventive fibers or fabrics are composed may have a heat distortion temperature at 66 psi determined by ASTM D 648 (with 0% nucleating agent) of about 95° C. or more, preferably greater than about 98° C., preferably greater than about 100° C., preferably greater than about 105° C.

Polymer microstructure is determined by $^{13}$C-NMR spectroscopy as described in the test methods section below, including the concentration of isotactic and syndiotactic diads ([m] and [r]), triads ([mm] and [rr]), and pentads ([mmmm] and [rrrr]). The designation "m" or "r" describes the stereochemistry of pairs of contiguous propylene groups, "m" referring to meso and "r" to racemic. The polymers present in propylene polymer composition useful in the fibers or fabrics of the present invention have some level of tacticity. Preferably, the polymers present in propylene polymer composition useful in the present invention have some level of isotacticity. Thus, in one embodiment of the invention, isotactic polypropylene is used in the propylene polymer compositions for the inventive fibers or fabrics. Similarly, highly isotactic polypropylene may be used in another embodiment of the inventive fibers or fabrics. As used herein, "isotactic" is defined as having at least 10% isotactic pentads according to analysis by $^{13}$C-NMR. As used herein, "highly isotactic" is defined as having at least 60% isotactic pentads according to analysis by $^{13}$C-NMR. In another embodiment of the invention, the composition comprising the fibers or fabrics may have an average meso run length MRL [defined by Eq. (16) below] as determined by $^{13}$C NMR (described in the Tests section) of higher than about 97, preferably higher than about 100, preferably higher than about 105, preferably 97 to 150, preferably 100 to 140, preferably 105 to 130.

In another embodiment of the invention, the polymer used in the propylene polymer compositions comprising the fibers or fabrics is syndiotactic, preferably highly syndiotactic. As used herein, "syndiotactic" is defined as having at least 10% syndiotactic pentads according to analysis by $^{13}$C-NMR. As used herein, "highly syndiotactic" is defined as having at least 60% syndiotactic pentads according to analysis by $^{13}$C-NMR.

In another embodiment of the invention, the propylene polymer compositions may comprise a blend of a tactic polymer with an atactic propylene polymer. Atactic polypropylene is defined to be less than 10% isotactic or syndiotactic pentads. Preferred atactic polypropylenes typically have an Mw of 10,000 up to 1,000,000 g/mol.

Useful propylene polymers for the manufacture of fibers or fabrics herein include those produced by metallocene catalyst systems including those propylene polymers having a composition distribution breadth index (CDBI) of 60% or more, preferably 70% or more, preferably 80% or more, preferably 90% or more. (CDBI is measured as described in WO 93/03093, with the modification that any fractions having a weight average molecular weight (Mw) below 25,000 g/mol are disregarded.)

In another embodiment of the invention, the inventive fibers or fabrics may be of a blend of a propylene polymer compositions, for example a polymer as defined herein having at least 50 mol % propylene with a MFR of 10 to 21.5 dg/min may be further blended with any polypropylene described herein, such as a homopolypropylene having an MFR of 22 dg/min or more, preferably 20 to 30 dg/min, preferably 22 to 28 dg/min, preferably about 25 dg/min. The propylene polymer compositions with a MFR of 10 to 21.5 dg/min may be present in such blends at from 1 wt % to 99 wt %, based upon the weight of the blend, preferably 5 wt % to 50 wt %, preferably 5 wt % to 25 wt %. Preferably the homopolypropylene having an MFR of 22 dg/min or more is present in the blend at 99 wt % to 1 wt %, based upon the weight of the blend (preferably at 95 to 50 wt %, preferably at 95 to 75 wt %) and the propylene polymer composition with a MFR of 10 to 21.5 dg/min is present in the blend at from 1 wt % to 99 wt %, based upon the weight of the blend, preferably 5 wt % to 50 wt %, preferably 5 wt % to 25 wt %.

Propylene Polymers Useful for Visbreaking

In a preferred embodiment of the invention the fibers or fabrics comprise a propylene polymer composition produced by visbreaking a base propylene polymer having an MFR of about 0.1 to about 8 dg/min. Base propylene polymers useful herein to produce the visbroken polymers include polypropylene homopolymers, polypropylene copolymers, and blends thereof. The homopolymer may be isotactic polypropylene, syndiotactic polypropylene or blends thereof (including blends with atactic polypropylene). The copolymer can be a random copolymer, a statistical copolymer, a block copolymer, or blends thereof. The method of making the base propylene polymer is not critical, as it can be made by slurry, solution, gas phase, a supercritical polymerization process as the one described in U.S. Pat. No. 7,807,769, a super-solution homogeneous polymerization process as the one described in US Patent Application Publication No. 2010/0113718 or other suitable processes, and by using catalyst systems appropriate for the polymerization of polyolefins, such as Ziegler-Natta-type catalysts, metallocene-type catalysts, other appropriate catalyst systems or combinations thereof. Such catalysts are well known in the art, and are described in, for example, ZIEGLER CATALYSTS (Gerhard Fink, Rolf Mülhaupt and Hans H. Brintzinger, Eds., Springer-Verlag 1995); Resconi et al., *Selectivity in Propene Polymerization with Metallocene Catalysts,* 100 CHEM. REV. 1253-1345 (2000); and I, II METALLOCENE-BASED POLYOLEFINS (Wiley & Sons 2000). In a preferred embodiment the base propylene polymers are made by the catalysts, activators and processes described in U.S. Pat. Nos. 6,342,566, 6,384,142, and 5741563; and PCT Publication Nos. WO 03/040201 and WO 97/19991.

In a preferred embodiment, the base propylene polymer can be a unimodal reactor grade, a bimodal reactor grade, an in-reactor blend or an extruder blend of two or more propylene polymers (for example a blend of MFR's of 0.8 dg/min and 2 dg/min) The base polymer may have a unimodal, bimodal, or multimodal molecular weight distribution (Mw/Mn) distribution of polymer species as determined by GPC. By bimodal or multimodal is meant that the GPC-SEC trace has more than one peak or inflection point. An inflection point is that point where the second derivative of the curve changes in sign (e.g., from negative to positive or vice versus). Typically the base polymer is visbroken to a final MFR preferably in the range of 10 to 25 dg/min, more preferably 14 to 19 dg/min. In another embodiment of the invention, the base polymer may not require peroxide cracking for increase of the MFR, as long as the in-reactor base polymer has desirable MFR (e.g. in the range of 10 to 25 dg/min and rheological characteristics). The composition could also be an extruder blend of two or more propylene polymers with or without peroxide cracking step, as long as combination of the key melt rheological parameters, crystallization and tacticity attributes are satisfied.

Preferred base propylene polymers useful to make the visbroken polymer for use in the fibers and fabrics of this invention typically have:

1. an Mw of 240,000 to 2,000,000 g/mol preferably 265,000 to 800,000, more preferably 3,000,000 to 600,000, as measured by the GPC method described in the tests method section; and/or
2. an Mw/Mn of 1 to 25, preferably 1.6 to 15, more preferably 2 to 8, more preferably 3 to 6 as measured by the GPC method described in the tests method section; and/or
3. a Tm (second melt, 1° C./min ramp speed, also referred to as "$T_{mp}$") of 100° C. to 200° C., preferably 120° C. to 185° C., preferably 130° C. to 175° C., more preferably 140° C. to 170° C., even more preferably 155° C. to 167° C., as measured by the DSC method described below in the test methods; and/or; and/or
4. a percent crystallinity (based on the heat of crystallization) of 20% to 80%, preferably 10% to 70, more preferably 35% to 55% as measured by the DSC method described below in the test methods; and/or 5. a glass transition temperature (Tg) of −50° C. to 120° C., preferably −20° C. to 100° C., more preferably −0° C. to 90° C. as determined by the DSC method described below in the test methods; and/or
6. a crystallization temperature (Tc 1° C./min ramp speed, also referred to as "$T_{cp}$") with 0% nucleating agent of 50° C. to 170° C., preferably 100° C. to 150° C., more preferably 110° C. to 145° C., preferably 115° C. to 135° C., as measured by the DSC method described below in the test methods; and/or
7. a branching index ($g'_{vis}$) of 0.85 or more, preferably 0.90 or more, preferably 0.95 or more, preferably 0.99 or more, as measured by the GPC method described in the test methods section; and/or
8. an MFR (ASTM 1238, 230° C., 2.16 kg) of 0.1 to 8 dg/min, preferably 0.5 to 5 dg/min, more preferably 0.8 to 3 dg/min), and/or
9. at least 10% tacticity (e.g. at least syndiotactic or at least 10% isotactic).

The base propylene homopolymer or propylene copolymer useful in the fibers and fabrics of the present invention preferably has some level of isotacticity. Thus, in one embodiment of the invention, isotactic polypropylene is used as the base propylene polymer herein. Similarly, highly isotactic polypropylene may be used in another embodiment as the base polymer. In another embodiment of the invention, the base propylene polymer may have an average meso run length MRL [defined by Eq. (16) below] as determined by $^{13}$C NMR (described in the test methods section) of higher than about 50, more preferably higher than about 80, more preferably higher than about 100, more preferably higher than about 105.

In another embodiment of the invention, the base propylene polymer useful herein is syndiotactic, preferably highly syndiotactic. As used herein, "syndiotactic" is defined as having at least 10% syndiotactic pentads according to analysis by $^{13}$C-NMR. As used herein, "highly syndiotactic" is defined as having at least 60% syndiotactic pentads according to analysis by $^{13}$C-NMR.

In another embodiment of the invention, the base propylene polymer useful herein may comprise a blend of a tactic polymer (such as isotactic polypropylene or highly isotactic polypropylene) with an atactic propylene polymer. Atactic polypropylene is defined to be less than 10% isotactic or syndiotactic pentads. Useful atactic polypropylenes typically have an Mw of 10,000 up to 1,000,000 g/mol.

Base propylene polymers useful herein include those produced by metallocene catalyst systems including those propylene polymers having a composition distribution breadth index (CDBI) of 60% or more, preferably 70% or more, preferably 80% or more, preferably 90% or more. (CDBI is measured as described in WO 93/03093, with the modification that any fractions having a weight average molecular weight (Mw) below 25,000 g/mol are disregarded.)

Visbreaking/Chain Scission

The terms "visbreaking" and "chain scission" are used interchangeably and are defined as the process of using one or more free radical initiators to increase polymer melt flow rate (MFR). This is described in U.S. Pat. No. 6,747,114 which is incorporated here by reference in its entirety. A "free radical initiator" is defined as a molecular fragment having one or more unpaired electrons.

In the context of this specification a polymer undergoes chain scission when the base polymer, or a blend of polymers, is treated with a free radical initiator, e.g., peroxide, preferably while the polymer is in a melted state, more preferably in a fully melted state. Preferably, the chain scission is controlled. For example, when a free radical initiator is used, free radicals of the polymers being treated are produced by thermal scission of the peroxide. Other sources of free radicals such as diazo compounds, oxygen or other compounds may also be utilized. In any case, it is contemplated that the free radicals produced from the initiator (e.g., peroxide) abstract the tertiary hydrogen on the propylene residue of the polymer. The resulting free radical disproportionates to two lower molecular weight chains, one with an olefin near the terminus and the other a saturated polymer. This process can continue with the generation of successively lower molecular weight polymers. Thus, under the appropriate conditions, chain scission is initiated to cause controlled degradation of the polymer or polymer blend.

Crosslinking is a competing process that may occur during chain scission. In a crosslinking reaction, the free radicals combine to form branched macromolecules of higher molecular weight. Eventually, this synthesis reaction may lead to vulcanization of the polymer. In copolymers of ethylene and propylene, this balance of crosslinking and degradation is mainly dependent on the composition of the copolymer. Since the degradation reaction is uniquely associated with the propylene residues, lower amounts of propylene in the copolymer tend to favor crosslinking over degradation. However, it should be recognized that the scission and crosslinking reactions are not mutually exclusionary. That is, even during degradation, some amount of branching may occur. In some cases the branching and scission reactions are random and do not lead to an increase in Mw/Mn. The amount of branching depends on a number of variables, primarily the reaction conditions, and the composition of the polymers and the extent of degradation. Random copolymers having a higher ethylene content should generate a higher level of branching than those with a lower ethylene content. Thus, the rate or extent of degradation may be substantially proportional to the relative amounts of propylene and ethylene sites. For example, if too many ethylene sites are present, the use of the peroxide or other free radical initiator may result in crosslinking rather than chain scission, and the material being treated will not degrade to a higher MFR. Thus, an important aspect of certain specific embodiments of the fibers and fabrics of this invention relates to the relative amounts of the polymers used in the blend. In blends of the base propylene polymers, these degradation processes occur for both of the polymers independently of each other.

The free-radical initiator, e.g., peroxide, may be added to the polymer while the polymer is in a solid form, e.g., by coating polymer pellets with an initiator, such as peroxide, which may be in powder, liquid, or other form, in which case the polymer is said to be "treated" with the initiator when the initiator becomes active, which usually happens at a temperature higher than melting point of the polymer. Preferably, however, the free-radical initiator is added to the polymer after the polymer has formed, but while the polymer is in a melted condition, e.g., during the post-polymerization processing, such as when a polymer mixture (which may include solvent) is introduced to a devolatalizer or extruder, which typically occurs at an elevated temperature.)

The term "melted" refers to the condition of the polymer when any portion of the polymer is melted, and includes fully melted and partially melted. Preferably, the polymer is treated by free-radical initiator while the temperature of the polymer is above its melting point.

In one method the visbreaking agent may be a peroxide, and an organic peroxide in another embodiment, wherein at least a methyl group or higher alkyl or aryl is bound to one or both oxygen atoms of the peroxide. In yet another method, the visbreaking agent may be a sterically hindered peroxide, wherein the alkyl or aryl group associated with each oxygen atom is at least a secondary carbon, a tertiary carbon in another embodiment. Non-limiting examples of sterically hindered peroxides ("visbreaking agents") include 2,5-bis (tert-butylperoxy)-2,5-dimethylhexane, 2,5-dimethyl-2,5-bis-(t-butylperoxy)-hexyne-3,4-methyl-4-t-butylperoxy-2-pentanone, 3,6,6,9,9-pentamethyl-3-(ethylacetate)-1,2,4,5-textraoxy cyclononane, and α,α'-bis-(tert-butylperoxy) diisopropyl benzene, and mixtures of these and any other secondary- or tertiary-hindered peroxides. A preferred peroxide is 2,5-bis(tert-butylperoxy)-2,5-dimethyl-hexane also known with the commercial name: Luperox 101 or Trigonox 101. Luperox 101 or Trigonox 101 can be fed in the extruder pure in liquid form or as a masterbatch blend in mineral oil (e.g. 50/50 weight/weight blend of Trigonox 101/mineral oil). Another common peroxide used as a visbreaking agent for polypropylene is di-t-amyl peroxide most commonly known with the commercial name DTAP. Alternatively, the free radical initiator may include a diazo compound, or any other compound or chemical that promotes free radicals in an amount sufficient to cause degradation as specified herein.

Preferred propylene polymers useful in the fibers and fabrics of this invention, include those that have been treated with a visbreaking agent such that its MFR is increased by at least 10%, preferably by at least 50% preferably by at least 100%, preferably by at least 300%, preferably by at least 500%, preferably by at least 650%. In the event the polymer is a blend of different propylene polymers, then an average MFR based on the logarithmic weight blending rule (Robeson, L. M., "Polymer Blends", Carl Hanser Verlag, Munich 2007, Chapter 6, p. 368) of the MFRs of the individual blend components is used to determine the MFR of the blend and was found to lead to excellent estimation of the blend MFR of the studied systems. For example, for a two component system, the ln(melt flow rate of the blend)=(weight fraction of component 1×ln(melt flow rate of component 1)+weight fraction of component 2×ln(melt flow rate of component 2). In another embodiment the visbroken polymer has an MFR that is from 10 to 25 units (dg/min) higher than the base polymer used to make the visbroken polymer, preferably 12 to 22 dg/min, preferably 14 to 19 dg/min Additives A variety of additives may be incorporated into the polymers and polymer blends described above used to make the fibers and fabrics for various purposes. Such additives include, for example, stabilizers, antioxidants, fillers, colorants, nucleating agents and slip additives. Primary and secondary antioxidants include, for example, hindered phenols, hindered amines, and phosphates. Nucleating agents include, for example, sodium benzoate, talc and other chemicals. Also, other nucleating agents may also be employed such as Ziegler-Natta olefin product or other highly crystalline polymer. Other additives such as dispersing agents, for example, Acrowax C, can also be included. Slip agents include, for example, oleamide and erucamide. Catalyst deactivators are also commonly used, for example, calcium stearate, hydrotalcite, calcium oxide, acid neutralizers, and other chemicals known in the art.

Other additives may include, for example, fire/flame retardants, plasticizers, curative agents, curative accelerators, cure retarders, processing aids, tackifying resins, and the like. The aforementioned additives of may also include fillers and/or reinforcing materials, either added independently or incorporated into an additive. Examples include carbon black, clay, talc, calcium carbonate, mica, silica, silicate, combinations thereof, and the like. Other additives which may be employed to enhance properties include antiblocking agents, lubricants, and nucleating agents. The lists described herein are not intended to be inclusive of all types of additives which may be employed with the present invention.

It is known that in the making of some meltspun fibers, surfactants and other active agents can be included in the polymer that is to be melt-processed. By way of example only, U.S. Pat. Nos. 3,973,068 and 4,070,218 teach a method of mixing a surfactant with the polymer and then melt-processing the mixture to form the desired fabric. The fabric is then treated in order to force the surfactant to the surface of the fibers. This is often done by heating the web on a series of heated rolls and is often referred to as "blooming" As a further example, U.S. Pat. No. 4,578,414 describes wettable olefin polymer fibers formed from a composition comprising a polyolefin and one or more surface-active agents. The surface-active agents are stated to bloom to the fiber surfaces where at least one of the surface-active agents remains partially embedded in the polymer matrix. In this regard, the permanence of wettability can be better controlled through the composition and concentration of the additive package. Still further, U.S. Pat. No. 4,923,914 to Nohr et al. teaches a surface-segregatable, melt-extrudable thermoplastic composition suitable for processing by melt extrusion to form a fiber or film having a differential, increasing concentration of an additive from the center of the fiber or film to the surface thereof. The differential, increasing concentration imparts the desired characteristic, e.g., hydrophilicity, to the surface of the fiber. As a particular example in Nohr, polyolefin fiber nonwoven webs are provided having improved wettability utilizing various polysiloxanes.

Of course, the particular active agent or agents included within one or more of the components can be selected as desired to impart or improve specific surface characteristics of the fiber and thereby modify the properties of the fabric made there from. A variety of active agents or chemical compounds have heretofore been utilized to impart or improve various surface properties including, but not limited to, absorbency, wettability, anti-static properties, anti-microbial properties, anti-fungal properties, liquid repellency (e.g. alcohol or water) and so forth. With regard to the wettability or absorbency of a particular fabric, many fabrics inherently exhibit good affinity or absorption characteristics for only specific liquids. For example, polyolefin nonwoven webs have heretofore been used to absorb oil or hydrocarbon based liquids. In this regard, polyolefin nonwoven wipes are inherently oleophilic and hydrophobic. Thus, polyolefin nonwoven fabrics can be treated in some manner in order to impart good wetting characteristics or absorbency for water or aqueous solutions or emulsions. As an example, exemplary wetting agents that can be melt-processed in order to impart improved wettability to the fiber include, but are not limited to, ethoxylated silicone surfactants, ethoxylated hydrocarbon surfactants, ethoxylated fluorocarbon surfactants and so forth. In addition, exemplary chemistries useful in making melt-processed thermoplastic fibers more hydrophilic are described in U.S. Pat. Nos. 3,973,068 and 4,070,218 to Weber et al. and U.S. Pat. No. 5,696,191 to Nohr et al.; the entire contents of the aforesaid references are incorporated herein by reference.

In a further aspect, it is often desirable to increase the barrier properties or repellency characteristics of a fabric for a particular liquid. As a specific example, it is often desirable in infection control products and medical apparel to provide a fabric that has good barrier or repellency properties for both water and alcohol. In this regard, the ability of thermoplastic fibers to better repel water or alcohol can be imparted by mixing a chemical composition having the desired repellency characteristics with the thermoplastic polymer resin prior to extrusion and thereafter melt-processing the mixture into one or more of the segments. The active agent migrates to the surface of the polymeric component thereby modifying the surface properties of the same. In addition, it is believed that the distance or gap between components exposed on the outer surface of the fiber containing significant levels of active agent is sufficiently small to allow the active agent to, in effect, modify the functional properties of the entire fiber and thereby obtain a fabric having the desired properties. Chemical compositions suitable for use in melt-extrusion processes and that improve alcohol repellency include, but are not limited to, fluorochemicals. Exemplary melt-processable liquid repellency agents include those available from DuPont under the trade name ZONYL fluorochemicals and also those available from 3M under the trade designation FX-1801. Various active agents suitable for imparting alcohol repellency to thermoplastic fibers are described in U.S. Pat. No. 5,145,727 to Potts et al., U.S. Pat. No. 4,855,360 to Duchesne et al., U.S. Pat. No. 4,863,983 to Johnson et al., U.S. Pat. No. 5,798,402 to Fitzgerald et al., U.S. Pat. No. 5,459,188 and U.S. Pat. No. 5,025,052; the entire contents of the aforesaid references are incorporated herein by reference. In addition to alcohol repellency, chemical compositions can be used to similarly improve the repellency or barrier properties for other low surface tension liquids. The above additives may be useful in fibers and fabrics of the invention to impart above discussed advantageous properties.

Inventive fibers and fabrics may further incorporate the residues of processing additives or excipients, for example, process oils or plasiticizers used to facilitate or improve processing of the polymers or polymer blends.

In manufacture of the fibers and fabrics, the blends of polymer compositions and additives may be prepared by any procedure that guarantees an intimate mixture of the components. For example, the components can be combined by melt pressing the components together on a Carver press to a thickness of 0.5 millimeter (20 mils) and a temperature of 180° C., rolling the resulting slab, folding the ends together and repeating the pressing, rolling, and folding operation 10 times. Internal mixers are particularly useful for solution or melt blending. Blending at a temperature of 180° C. to 240° C. in a Brabender Plastograph for 1 to 20 minutes has been found satisfactory. Still another method that may be used for admixing the components involves blending the polymers in a Banbury internal mixer above the flux temperature of all of the components, e.g., 180° C. for 5 minutes. These processes are well known in the art and include single and twin screw mixing extruders, static mixers for mixing molten polymer streams of low viscosity, and impingement mixers.

The blends may be prepared by any procedure that produces a mixture of the components, e.g., dry blending, melt blending, etc. In certain embodiments, a complete mixture of the polymeric components is indicated by the uniformity of the morphology of the dispersion of the polymer components.

Melt blend: Continuous melt mixing equipment are generally used. These processes are well known in the art and include single and twin screw compounding extruders as well as other machines and processes, designed to homogenize the polymer components intimately.

Dry blend: The polymers and other component may be dry blended and fed directly into the fiber or nonwoven process extruders. Dry blending is accomplished by combining polymers and other ingredients in dry blending equipment. Such equipment and processes are well known in the art and include a drum tumbler, a double cone blender, etc. In this case, polymer and other ingredients are melted and homogenized in the process extruder similar to the melt blend process. Instead of making the pellets, the homogenized molten polymer is delivered to the die or spinneret to form the fiber, fabric, film, sheet or molded article.

Fiber and Fabric Formation

The formation of nonwoven fabrics from polyolefins and their blends generally requires the manufacture of fibers by extrusion followed by consolidation or bonding. The extrusion process is typically accompanied by mechanical or aerodynamic drawing of the fibers. The fabric of the present invention may be manufactured by any technique known in the art. Such methods and equipment are well known. For example, spunbond nonwoven fabrics may be produced by spunbond nonwoven production lines produced by Reifenhäuser GmbH & Co., of Troisdorf, Germany. This utilizes a slot drawing technique as described in U.S. Pat. No. 4,820,142, EP 1340 843 A1 or U.S. Pat. No. 6,918,750. Additional useful methods include those disclosed in US 2012/0116338 A1 and US 2010/0233928 A1.

Illustrative fabric basis weights of the fabrics of the invention are in the range of 5 to 70 gsm, preferably from 5 to 50 gsm, preferably from 5 to 25 gsm, more preferably from 5 to 20 gsm, especially from 5 to 15 gsm, more preferably 7 to 15 gsm, for example 12 gsm.

In certain embodiments fabrics of the invention as defined in any claim herein have any one or more of the following:
a tensile strength anisotropy defined as the ratio of the specific tensile strength in the MD over the specific tensile strength in the CD of less than about 2.7;
a total hand of less than about 6.8 gr;
a MD tensile modulus (as defined herein) of less than about 35 N/5 cm/gsm;
a CD specific tensile strength of at least 1.0 N/5 cm/gsm, preferably at least 1.1N/5 cm/gsm, a MD specific tensile strength of at least 2.7 N/5 cm/gsm, preferably at least 2.9 N/5 cm/gsm, and a total hand of less than about 6.8 gm force, preferably less than about 6.6 gm force, or a tensile modulus of less than about 32 N/5 cm/gsm, preferably less than about 30 N/5 cm/gsm; a fabric tensile anisotropy (ratio of MD over CD specific tensile strength as defined herein) of less than about 2.7;

In one advantageous embodiment, the nonwoven fabric comprises polypropylene fibers of
a propylene polymer having:
a) a melt flow rate (MFR, ASTM 1238, 230° C., 2.16 kg) of about 14 dg/min to about 19 dg/min;
b) a dimensionless Stress Ratio/Loss Tangent Index $R_2$ [defined by Eq. (8) herein] at 190° C. from about 2.5 to about 6.5;
c) an onset temperature of crystallization under flow, $T_{c,rheol}$, (as determined by SAOS rheology, 1° C./min as described below, where said polymer has 0 wt % nucleating agent present), of at least about 136° C.; and
d) an average meso run length determined by $^{13}C$ NMR of from 97 to 140.

In certain preferred fabrics of the invention the fibers have a dpf value of from 0.3 to 5 dpf. The polypropylene fibers of the fabrics of the invention are preferably monofilaments, which preferably have a denier value of from 0.3 to 5 denier.

Nonwoven fabrics of the invention may comprise a single layer or a plurality of layers, for example a plurality of nonwoven layers that are bonded together. The fabrics of the invention may be for example spunbonded nonwovens or meltblown nonwovens, with spunbonded nonwovens being especially preferred. Where a nonwoven fabric of the invention is used in a laminate with one or more other fabric, the other fabric or fabrics may be a fabric of this invention or may be another fabric. The invention provides in particular a laminate comprising a plurality of nonwoven fabrics according to the present invention, which may if desired be bonded together. Laminates may include a plurality of nonwovens selected from spunbonded nonwovens and meltblown nonwovens optionally with one or more further fabrics. The fabrics may be used alone or in combination with other fabrics in a wide variety of applications as hereinafter described.

As already mentioned the polypropylene fibers of the fabrics of the invention comprise a propylene polymer comprising at least 50 mol % propylene. It is preferred that the said propylene polymer comprises at least 60 mol %, preferably at least 70 mol %, more preferably at least 80 mol %, for example at least 90 mol % units derived from propylene. Further, fabrics of the invention may if desired comprise fibers of a propylene polymer composition comprising a combination of two or more propylene polymers as disclosed under "Polymer compositions" above.

In certain embodiments the polypropylene fibers are present in an amount of at least 50% by weight, preferably at least 75% by weight, more preferably at least 85% by weight, based on the total weight of fibers in said nonwoven fabric.

The fabrics of the invention are obtainable at high production line speeds with low occurrence of breakage. For example, the fabrics may in some embodiments be obtainable at production line speeds of at least 400 m/min, preferably at least 600 m/min, preferably at least 750 m/min, for example at 900 m/min. Even at high production line speeds good spinnability is obtained, allowing fine filaments to be formed reliably with minimal filament breakage.

Fine Denier Fibers

Fibers of the invention may be for example continuous filament, bulked continuous filament, and staple. Fibers of this invention can be used with advantage in the manufacture of non-wovens. Non-wovens made using fibers of this invention have excellent properties including high strength at low fabric base weights. Fibers of this invention are fine fibers with excellent mechanical strength, allowing formation of a non-woven of low base weight which has excellent mechanical properties notwithstanding the low fabric base weight. Fibers of the invention preferably have a dpf value of 0.3 to 5 dpf. In some embodiments the fibers may be yarns comprising a plurality of fibers with a dpf value of 0.3 to 5 dpf. In other embodiments the fiber may be a monofilaments of 0.3 to 5 denier. When used in nonwoven fabrics it is preferred that the fibers are monofilaments. In an illustrative method of making fine denier fibers, the polymer melt is extruded through the holes in the die (spinneret) between, 0.3 mm to 0.8 mm in diameter. Low melt viscosity of the polymer is important and is achieved through the use of high melt temperature (230° C. to 280° C.) and high melt flow rates (e.g. 10 g/10 min to 40 g/10 min) of the polymers used. A relatively large extruder is usually equipped with a manifold to distribute a high output of molten PP to a bank of two to fifty (alternately eight to twenty) spinnerets. Each spinhead is usually equipped with a separate gear pump to regulate output through that spinhead; a filter pack, supported by a "breaker plate;" and the spinneret plate within the head. The same technique may be adapted to form yarns. The number of holes in the spinneret plate determines the number of filaments in a yarn and varies considerably with the different yarn constructions, but it is typically in the range of 50 to 250. The holes are typically grouped into round, annular, or rectangular patterns to assist in good distribution of the quench air flow.

Continuous Filament

Continuous filament yarns typically range from 40 denier to 2,000 denier (denier=number of grams/9000 meters). Filaments can range from 1 to 20 denier per filament (dpf) and the range is expanding. Spinning speeds are typically 10 to 10,000 m/min (alternately 800 m/min to 1500 m/min) An exemplary method would proceed as follows. The filaments are drawn at draw ratios of 3:1 or more (one- or two-stage draw) and wound onto a package. Two-stage drawing allows higher draw ratios to be achieved. Winding speeds are of 2,000 m/min or more, alternately 3,500 m/min or more are useful.

Partially Oriented Yarn (POY)

Partially oriented yarn (POY) is the fiber produced directly from fiber spinning without solid state drawing (as continuous filament mentioned above). The orientation of the molecules in the fiber is done only in the melt state after the molten polymer leaves the spinneret. Once the fiber is solidified, little or no drawing of the fiber takes place and the fiber is wounded up into a package. The POY yarn (as opposed to fully oriented yarn, or FOY, which has gone through solid state orientation and has a higher tensile strength and lower elongation) tends to have a higher elongation and lower tenacity.

Bulked Continuous Filament

Bulked Continuous Filament ("CF") fabrication processes fall into two basic types, one-step and two steps. For example, in a two-step process, an undrawn yarn is spun at less than 1,000 m/min (3,300 ft/min), usually 750 m/min, and placed on a package. The yarn is drawn (usually in two stages) and "bulked" on a machine called a texturizer. Winding and drawing speeds are limited by the bulking or texturizing device to 2,500 m/min (8,200 ft/min) or less. A common process today is the one-step spin/draw/text (SDT) process. It is similar to the one-step CF process, except that the bulking device is in-line. Bulk or texture changes yarn appearance, separating filaments and adding enough gentle bends and folds to make the yarn appear fatter (bulkier).

Staple Fiber

There are two basic staple fiber fabrication processes: traditional and compact spinning. The traditional process typically involves two steps: 1) producing, applying finish, and winding followed by 2) drawing, a secondary finish application, crimping, and cutting into staple. Filaments can range, for example, from 0.5 dpf to >70 dpf, (dpf=denier per filament) depending on the application. Staple length can be as short as 3 mm or as long as 200 mm (0.25 in. to 8 in.) to suit the application. For many applications the fibers are crimped. Crimping is accomplished by over-feeding the tow into a steam-heated stuffer box with a pair of nip rolls. The overfeed folds the tow in the box, forming bends or crimps in the filaments. These bends are heat-set by steam injected into the box.

Meltblown Fabrics

Meltblown fibers are fibers formed by extruding a molten thermoplastic material through a plurality of fine, usually circular, die capillaries as molten threads or filaments into usually converging, usually hot and high velocity, gas, e.g. air, streams to attenuate the filaments of molten thermoplastic material to form fibers. During the meltblowing process, the diameter of the molten filaments is reduced by the drawing air to a desired size. Thereafter, the meltblown fibers are carried by the high velocity gas stream and are deposited on a collecting surface to form a web of substantially randomly disbursed meltblown fibers. Such a process is disclosed, for example, in U.S. Pat. No. 3,849,241 to Buntin et al., U.S. Pat. No. 4,526,733 to Lau, and U.S. Pat. No. 5,160,746 to Dodge, II et al., all of which are hereby incorporated herein by this reference. Meltblown fibers may be continuous or discontinuous and are generally smaller than ten microns in average diameter.

In a conventional meltblowing process, molten polymer is provided to a die that is disposed between a pair of air plates that form a primary air nozzle. Standard meltblown equipment includes a die tip with a single row of capillaries along a knife edge. Typical die tips have approximately 30 capillary exit holes per linear inch of die width. The die tip is typically a 60° wedge-shaped block converging at the knife edge at the point where the capillaries are located. The air plates in many known meltblowing nozzles are mounted in a recessed configuration such that the tip of the die is set back from the primary air nozzle. However, air plates in some nozzles are mounted in a flush configuration where the air plate ends are in the same horizontal plane as the die tip; in other nozzles the die tip is in a protruding or "stick-out" configuration so that the tip of the die extends past the ends of the air plates. Moreover, as disclosed in U.S. Pat. No. 5,160,746 to Dodge II et al., more than one air flow stream can be provided for use in the nozzle.

In some known configurations of meltblowing nozzles, hot air is provided through the primary air nozzle formed on each side of the die tip. The hot air heats the die and thus prevents the die from freezing as the molten polymer exits and cools. In this way the die is prevented from becoming clogged with solidifying polymer. The hot air also draws, or attenuates, the melt into fibers. Other schemes for preventing freezing of the die, such as that detailed in U.S. Pat. No. 5,196,207 to Koenig, using heated gas to maintain polymer temperature in the reservoir, is also known. Secondary, or quenching, air at temperatures above ambient is known to be provided through the die head, as in U.S. Pat. No. 6,001,303 to Haynes et al. Primary hot air flow rates typically range from about 20 to 24 standard cubic ft. per minute per in. of die width (SCFM/in).

Primary air pressure typically ranges from 5 to 10 pounds per square inch gauge (psig) at a point in the die head just prior to exit. Primary air temperature typically ranges from about 232° C. to about 315° C., but temperatures of about 398° C. are not uncommon. The particular temperature of the primary hot air flow will depend on the particular polymer being drawn as well as other characteristics desired in the meltblown web.

Expressed in terms of the amount of polymer material flowing per inch of the die per unit of time, polymer throughput is typically 0.5 to 1.25 grams per hole per minute (ghm). Thus, for a die having 30 holes per inch, polymer throughput is typically about 2 to 5 lbs/in/hr (PIH).

Moreover, in order to form meltblown fibers from an input of about five pounds per inch per hour of the polymer melt, about one hundred pounds per inch per hour of hot air is required to draw or attenuate the melt into discrete fibers. This drawing air must be heated to a temperature on the order of about 204° C. to about 315° C. in order to maintain proper heat to the die tip.

Because such high temperatures must be used, a substantial amount of heat is typically removed from the fibers in order to quench, or solidify, the fibers leaving the die orifice. Cold gases, such as air, have been used to accelerate cooling and solidification of the meltblown fibers. In particular, in U.S. Pat. No. 5,075,068 to Milligan et al. and U.S. Pat. No. 5,080,569 to Gubernick et al., secondary air flowing in a cross-flow perpendicular, or 90°, direction relative to the direction of fiber elongation, has been used to quench meltblown fibers and produce smaller diameter fibers. In addition, U.S. Pat. No. 5,607,701 to Allen et al. uses a cooler pressurized quench air that fills chamber 71 and results in faster cooling and solidification of the fibers. In U.S. Pat. No. 4,112,159 to Pall, a cold air flow is used to attenuate the fibers when it is desired to decrease the attenuation of the fibers.

Through the control of air and die tip temperatures, air pressure, and polymer feed rate, the diameter of the fiber formed during the meltblown process may be regulated. For example, typical meltblown polypropylene fibers have a diameter of 3 to 4 microns.

After cooling, the fibers are collected to form a nonwoven web. In particular, the fibers are collected on a forming web that comprises a moving mesh screen or belt located below the die tip. In order to provide enough space beneath the die tip for fiber forming, attenuation and cooling, forming distances of at least about 8 to 12 inches between the polymer die tip and the top of the mesh screen are required in the typical meltblowing process.

However, forming distances as low as 4 inches are described in U.S. Pat. No. 4,526,733 to Lau (hereafter the Lau patent). As described in Example 3 of the Lau patent, the shorter forming distances are achieved with attenuating air flows of at least about 37° C. cooler than the temperature of the molten polymer. For example, the Lau patent discloses the use of attenuating air at about 65° C. for polypropylene melt at a temperature of about 266° C. to allow a forming distance between die tip and forming belt of 4 inches. The Lau patent incorporates passive air gaps 36 (shown in FIG. 4 of the Lau patent) to insulate the die tip.

In a preferred embodiment, melt blown fibers are produced with the polymers described herein. In the melt blown process molten polymer moves from the extruder to the special melt blowing die. As the molten filaments exit the die, they are contacted by high temperature, high velocity air (called process or primary air). This air rapidly draws and, in combination with the quench air, solidifies the filaments. The entire fiber forming process generally takes place within 7 mm (0.25 in.) from the spinnerets. The fabric is formed by blowing the filaments directly onto a forming wire, 200 mm to 400 mm (8 in. to 15 in.) from the spinnerets. Melt blown microfibers useful in the present invention can be prepared as described in Van A. Wente, "Superfine Thermoplastic Fibers," Industrial Engineering Chemistry, vol. 48, pp. 1342-1346 and in Report No. 4364 of the Naval Research Laboratories, published May 25, 1954, entitled "Manufacture of Super Fine Organic Fibers" by Van A. Wente et al.

Spunbonded Fabrics

A particular embodiment of the present invention relates to spunbonded fabrics. Conventional spunbond processes are illustrated in U.S. Pat. Nos. 3,825,379; 4,813,864; 4,405,297; 4,208,366; and 4,334,340 all hereby incorporated by reference for purposes of U.S. patent practice. The spunbonding process is one which is well known in the art of fabric production. Generally, continuous fibers are extruded, laid on an endless belt, and then bonded to each other, and often times to a second layer such as a melt blown layer, often by a heated calender roll, or addition of a binder. An overview of spunbonding may be obtained from L. C. Wadsworth and B. C. Goswami, Nonwoven Fabrics: "Spunbonded and Melt Blown Processes" proceedings Eight Annual Nonwovens Workshop, Jul. 30-Aug. 3, 1990, sponsored by TANDEC, University of Knoxville, Tenn.

A typical spunbond process consists of a continuous filament extrusion, followed by drawing, web formation by the use of some type of ejector, and bonding of the web. First, in one embodiment of the invention, a spunbonded nonwoven is obtainable from a propylene based polymer having an MFR of 10-25 dg/min (or a propylene polymer that has been visbroken to have an MFR of 10 to 25 dg/min) in pellet form. The pelletized 10-25 dg/min MFR propylene based resin is then fed into an extruder. In the extruder, the pellets simultaneously are melted and forced through the system by a heating melting screw. At the end of the screw, a spinning pump meters the melted polymer through a filter to a spinneret where the melted polymer is extruded under pressure through capillaries, at a rate of 0.3-1.0 grams per hole per minute. The spinneret contains a several thousand capillaries, typically measuring 0.4-0.6 mm in diameter. The polymer is melted at about 30° C. to 100° C., typically 50 to 100° C. above its melting point to achieve sufficiently low melt viscosity for extrusion. The fibers exiting the spinneret are quenched and drawn into fine fibers measuring 10-40 microns in diameter by cold, high velocity air jets. The solidified fiber is laid randomly on a moving belt to form a random netlike structure known in the art as web. After web formation the web is bonded to achieve its final strength using heated textile calenders known in the art as thermo bond calenders. The calenders consists of two heated steel rolls; one roll is plain and the other bears a pattern of raised points. The web is conveyed to the calender wherein a fabric is formed by pressing the web between the rolls at a bonding temperature of about 100° C. to 200° C.

While bonding occurs within a wide temperature range the bonding temperature must be optimized for achieving a fabric having maximum mechanical strength. Over bonding, that is, bonding at a temperature greater than optimum results in fibers having significantly weaker fiber around the bonding point because of excessive melting of the fiber. These become the weak points in the fabric. Under bonding, that is, bonding at a temperature lower than the optimum results in insufficient bonding at the fiber-to-fiber links. The optimum bonding temperature depends upon the nature of the material that the fibers are made of. The bonding area of fabrics of the invention, as is known to those of ordinary skill in the art is dependent on the roll surface configuration, and is preferably from 10 to 30%, more preferably from 15 to 30%, especially from 15 to 28%, more especially from 17 to 23%.

Annealing

Another part of the invention is that the mechanical properties referred to above can be obtained by the annealing the polymer fiber. Annealing is often combined with mechanical orientation. It is preferred to employ an annealing step in the process. Annealing may also be done after fabrication of a non-woven material from the fibers. Annealing partially relieves the internal stress in the stretched fiber and restores the elastic recovery properties of the blend in the fiber. Annealing has been shown to lead to significant changes in the internal organization of the crystalline structure and the relative ordering of the amorphous and semicrystalline phases. This leads to recovery of the elastic properties. Thermal annealing of the polymer blend is conducted by maintaining the polymer blends or the fibers or fabrics at a temperature between room temperature to a maximum of 160° C. or more preferably to a maximum of 130° C. for a period between 5 minutes to less than 7 days. A typical annealing period is 3 days at 50° C. or 5 minutes at 100° C. The annealing time and temperature can be adjusted for any particular blend composition by experimentation. While the annealing is done in the absence of mechanical orientation, the latter can be a part of the annealing process on the fiber (past the extrusion operation) required to produce an elastic material. Mechanical orientation can be done by the temporary, forced extension of the polymer fiber for a short period of time before it is allowed to relax in the absence of the extensional forces. Oriented polymer fibers are obtained by maintaining the polymer fibers or the articles made from a blend at an extension of 100% to 700% for a period of 0.1 seconds to 24 hours. A typical orientation is an extension of 200% for a momentary period at room temperature.

For orientation, a polymeric fiber at an elevated temperature (but below the crystalline melting point of the polymer) is passed from a feed roll of fiber around two rollers driven at different surface speeds and finally to a take-up roller. The driven roller closest to the take-up roll is driven faster than the driven roller closest to the feed roll, such that the fiber is stretched between the driven rollers. The assembly may include a roller intermediate the second roller and take-up roller to cool the fiber. The second roller and the take-up roller may be driven at the same peripheral speeds to maintain the fiber in the stretched condition. If supplementary cooling is not used, the fiber will cool to ambient temperature on the take up roll.

In other embodiments, the nonwoven fabrics of the present invention require little to no post fabrication processing. In another embodiment, the fabrics of the present invention are annealed in a single-step by a heated roll (godet) during calendering under low tension. Depending on the end use application, it is apparent what techniques are appropriate and what variations in process parameters are required to obtain the desired fabric properties.

Devices and methods to convert the compositions described herein into fibers and fabrics are known in the art, see for example to EP 1340 843 A1.

Useful inventive fabrics are obtainable using an apparatus for the continuous production of a spunbonded web of filaments, with spinneret, a cooling chamber in which the process air for cooling filaments can be inserted, a monomer exhaust device located between spinneret and cooling chamber, a stretching unit and a deposit device for depositing the filaments to spunbonded nonwoven fabric, wherein the cooling chamber is divided into two cooling chamber sections, wherein process air from a first upper cooling chamber section with a volume flow VM can be pulled (such as with a vacuum) to the monomer exhaust device, said process air from the first upper cooling chamber section with a volume flow V1 escaping into a second lower cooling chamber section and said volume flow ratio is VM/V1 0.1 to 0.3, preferably 0.12 to 0.25.

Especially preferred volume flow ratio is from 0.15 to 0.2 VM/V1. The flow rate is appropriately measured in $m^3/s$. The term process air refers in particular to cooling air for filament cooling. Preferably, the filaments are stretched aerodynamically in the stretching unit. It is preferred that the filaments are produced as monocomponent filaments. In principle also bicomponent filaments or multicomponent filaments can also be produced.

It is preferred that process air with a volume flow V2 escapes from the second lower cooling chamber section and that the volume flow ratio of the volume flow V1 escaping from the first upper cooling chamber section to the volume flow V2 (V1/V2) escaping from the second lower cooling chamber section is from 0 to 0.5, preferably 0.05 to 0.5 and particularly preferably 0.1 to 0.45. In one possible arrangement, the filaments escaping from the second lower cooling chamber section and the process air escaping from second lower cooling chamber section are introduced into the stretching unit.

It is preferred that process air from the first upper cooling chamber section is escaping with a speed v1 into the second lower cooling chamber section, that process air is escaping from the second lower cooling chamber section with a speed v2 and that the speed ratio v1/v2 is 0.2 to 0.5, preferably 0.25 to 0.5 and preferentially 0.3 to 0.5. In another variant the speed ratio v1/v2 is from 0.35 to 0.45 and in particular for example 0.4. Between the cooling chamber and the stretching unit an intermediate passage may be located. The intermediate channel from the outlet of the cooling chamber to the inlet of a covert channel of the stretching unit is converging wedge-shaped in the vertical section. Conveniently, the intermediate channel converges wedge-shaped to the inlet of the covert channel in the vertical section on the entrance width of the drawing channel. In the manufacture of certain spunbond fabrics of the invention there is no air supply provided in the range of the cooling chamber and in the transition region between the cooling chamber and stretching unit, apart from the supply of process air in the cooling chamber. In that regard the invention works with a closed system. Preferably, in the section of the cooling chamber, in the region of the intermediate channel and in the region of stretching unit no air supply from outside will be provided, apart from the supply of process air in the cooling chamber. It is recommended that at least one diffuser should be arranged between the stretching unit and the storage device. Such a diffuser advantageously has a storage device oriented toward the diverging section or a section with diverging side walls. As a result a fail-safe deposition of the filaments to non-uniform web is easier. Preferably the depositing apparatus is an endlessly circulating conveyer belt. The filaments are deposited on this conveyer belt for spunbonded nonwoven fabric and the fabric is subsequently suitably compacted and/or consolidated, preferably the consolidation occurs in a calender.

In one suitable process for continuous production of a spunbonded nonwoven fabric of the invention, the filaments are spun through a spinneret and guided past the monomer exhaust device into a cooling chamber, the filaments are cooled in the cooling chamber with process air, the cooling chamber is divided into two cooling chamber sections, and process air from a first upper cooling chamber section with a volume flow VM can be pulled (such as with a vacuum) to the monomer exhaust device, said process air from the first upper cooling chamber section with a volume flow V1 exiting in a second lower cooling chamber section and said volume flow ratio being VM/V1 0.1 to 0.3, preferably 0.12 to 0.25, wherein the filaments after leaving the cooling chamber are introduced into a stretching unit and wherein the filaments then deposited on a conveyer belt for the spunbonded nonwoven fabric.

It is within the scope of the invention that the filaments in a nonwoven fabric of this invention are present as monocomponent filaments.

It is also within the scope of the invention that the filaments in the spunbonded fabrics of this invention are drawn. Drawing of the filaments is carried out to obtain a filament diameter from 0.3 to 5, alternately from 0.3 to 2 denier, alternately from 0.3 to 0.9 denier. Conveniently, the filament diameter of the filaments is smaller than 3 denier, alternately small than 2.5 denier, alternately smaller than 2 denier, alternately smaller than 1 denier. The filament diameter is measured at the spunbonded nonwoven fabric deposited filaments.

In a preferred embodiment, any of the fabrics (such as nonwoven fabrics) according to this invention have a CD specific tensile strength (determined from the peak load of the force-elongation curve as measured by Worldwide Strategic Partners test 110.4(5) (WSP 110.4 (05)) of at least 1 N/5 cm/gsm, preferably at least 1.1 N/5 cm/gsm, preferably at least 1.2 N/5 cm, for a fabric basis weight in the range of 8 to 12 gsm produced at a line speed of at least 600 m/min and more preferably at least 700 m/min and more preferably of at least 800 m/min. CD specific tensile strength (N/5 cm/gsm) is CD strength (N/5 cm) divided by fabric basis weight (gsm) (normalization).

In a preferred embodiment, any fabric (such as nonwoven fabric) according to this invention has a MD specific tensile strength (as measured by WSP 110.4 (05)) of at least 2.7 N/5 cm/gsm, preferably at least 2.9 N/5 cm/gsm, preferably 3.0 N/5 cm/gsm, for a fabric basis weight in the range of 8 to 12 gsm produced at a line speed of at least 600 m/min and more preferably at least 700 m/min and more preferably of at least 800 m/min. MD specific tensile strength (N/5 cm/gsm) is MD strength (N/5 cm) divided by fabric basis weight (gsm) (normalization).

In a preferred embodiment, any of the fabrics (such as nonwoven fabrics) according to this invention have a tensile strength anisotropy defined as the ratio of the specific tensile strength in the MD over the CD (as measured by WSP 110.4 (05)) of less than about 2.7 preferably less than about 2.6, preferably less than about 2.6 for a fabric basis weight in the range of 8 to 12 gsm produced at a line speed of at least 600 m/min and more preferably at least 700 m/min and more preferably of at least 800 m/min.

In a preferred embodiment, any of the inventive fabrics or other fabrics containing fibers of this invention (such as nonwoven fabrics) have a total hand (determined as described in the Test Methods below) of less than about 6.8 gr, preferably less than about 6.6 gr, preferably less than about 6.5 gr for a fabric basis weight in the range 8 to 12 gsm produced at a line speed of at least 600 m/min and more preferably at least 700 m/min and more preferably of at least 800 m/min. Preferably the fabrics made herein have a total hand of less than about 6.8 gr and more preferably less than about 6.5 gr.

In a preferred embodiment, any of the of the inventive fabrics or other fabrics containing fibers of this invention (such as nonwoven fabrics) prepared according to this invention have a MD tensile modulus (determined as described in the Test Methods below) of less than about 35 N/5 cm/gsm, preferably less than about 32 N/5 cm/gsm, preferably less than about 30 N/5 cm/gsm, for a fabric basis weight in the range of 8 to 12 gsm produced at a line speed of at least 600 m/min and more preferably at least 700 m/min and more preferably of at least 800 m/min.

In a particularly preferred embodiment, compositions which characterize the fabrics and fibers of this invention have good spinnability (as defined above) in combination with outstanding fiber tensile properties and/or fabric tensile properties when used in fabrics (e.g. CD specific tensile strength of at least 1.1 N/5 cm/gsm, a MD specific tensile strength of at least 2.7 N/5 cm/gsm and a total hand of less than about 6.8 gm force or a tensile modulus of less than about 32 N/5 cm/gsm, for a fabric basis weight in the range of 8 to 12 gsm produced at a line speed of at least 600 m/min and more preferably at least 700 m/min and more preferably of at least 800 m/min.

In a particularly preferred embodiment, compositions which characterize the fabrics and fibers of this invention have good spinnability (as defined above) in combination, when used in the inventive fabrics, with a fabric tensile anisotropy (ratio of MD over CD specific tensile strength as determined by WSP 110.4 (05)) of less than about 2.7, for a fabric basis weight in the range of 8 to 12 gsm produced at a line speed of at least 600 m/min and more preferably at least 700 m/min and more preferably of at least 800 m/min.

In a particularly preferred embodiment, compositions which characterize the fabrics and fibers of this invention have good spinnability (as defined above) in combination with, when used in the inventive fabrics, outstanding fabric tensile properties (e.g. CD specific tensile strength of at least 1.2 N/5 cm/gsm, MD specific tensile strength of at least 2.9 N/5 cm/gsm, and total hand of less than about 6.6 gm force or MD tensile modulus of less than about 30 N/5 cm/gsm, for a fabric basis weight in the range of 8 to 12 gsm produced at a line speed of at least 600 m/min and more preferably at least 700 m/min and more preferably of at least 800 m/min.

In a particularly preferred embodiment, the compositions which characterize the fibers and fabrics of the invention have excellent spinnability (e.g. stable fabrication without breaks) particularly when thin (e.g. less than 18 microns or equivalently less than about 2 denier) fibers are made.

In another preferred embodiment, fabrics (such as nonwoven fabrics) made using the materials described herein have a: 1) A ratio of CD elongation to CD peak strength of 40 or more, when measured at speed of 200 mm/min and 100 mm gauge length (WSP110.4 (0.5)), preferably 45 or more; and 2) a CD strength of Y N/5 cm/gsm or more, where Y=−0.0005 (X)+1.46 (preferably 1.48, preferably 1.5, preferably 1.6), where X is the production line speed of the fabric is at least 400 m/min, provided the CD strength is at least 1.0 N/5 cm/gsm. CD peak elongation (also referred to as CD elongation), and CD peak strength (also referred to as CD strength) are determined according to WSP 110.4 (05), using a gauge length of 200 mm and a testing speed of 100 mm/min unless otherwise indicated.

In an other preferred embodiment, fabrics (such as nonwoven fabrics) made using the materials described herein have a CD strength of Y N/5 cm/gsm or more, where Y=−0.0009(X)+1.965 (preferably 2.1, preferably 2.3), where X is the production line speed of the fabric and is at least 400 m/min. CD strength is determined according to WSP 110.4 (05), using a gauge length of 200 mm and a testing speed of 100 mm/min.

In another preferred embodiment, fabrics (such as nonwoven fabrics) made using the materials described herein have a CD strength of Y N/5 cm/gsm or more, where Y=−0.0008(X)+1.85 (preferably 1.95), where X is the production line speed of the fabric and is at least 400 m/min CD strength is determined according to WSP 110.4 (05), using a gauge length of 200 mm and a testing speed of 100 mm/min.

In another preferred embodiment, fabrics (such as nonwoven fabrics) made using the materials described herein have a MD strength of Y N/5 cm/gsm or more, where Y=−0.0007(X)+2.145 (preferably 2.4), where X is the production line speed of the fabric and is at least 400 m/min MD strength (also referred to as MD peak strength) is determined according to WSP 110.4 (05), using a gauge length of 00 mm and a testing speed of 100 mm/min.

In another preferred embodiment, fabrics (such as nonwoven fabrics) made using the materials described herein have a MD strength of Y N/5 cm/gsm or more, where Y=−0.0006(X)+2.34 (preferably 2.4, preferably 2.5), where X is the production line speed of the fabric and is at least 400 m/min. MD strength (also referred to as MD peak strength) is determined according to WSP 110.4 (05), using a gauge length of 200 mm and a testing speed of 100 mm/min.

In another preferred embodiment, fabrics (such as nonwoven fabrics) made using the materials described herein have a MD strength of Y N/5 cm/gsm or more, where Y=−0.0007(X)+2.715 (preferably 2.8, preferably 2.9), where X is the production line speed of the fabric and is at least 400 m/min. MD strength (also referred to as MD peak strength) is determined according to WSP 110.4 (05), using a gauge length of 200 mm and a testing speed of 100 mm/min.

In another preferred embodiment, fabrics (such as nonwoven fabrics) made using the materials described herein have are produced at a line speed of at least 500 m/min (preferably at least 600 m/min, at least 700 m/min, at least 800 m/min, at least 850 m/min, at least 900 m/min)

INDUSTRIAL APPLICABILITY

The fibers and fabrics of the invention have wide applicability spanning several industries. For example, fabrics of the invention may be used in the manufacture of hygiene products. Examples include diapers and feminine hygiene products. The fabrics of the invention are also useful for medical products. Examples include medical fabric for gowns, linens, towels, bandages, instrument wraps, scrubs, masks, head wraps, and drapes. Additionally, the fabrics of the invention are useful in the manufacture of consumer products. Examples include seat covers, domestic linens, tablecloths, and car covers. It is also contemplated that the inventive fabrics may make-up either a portion or a component of the articles described above.

The fibers and nonwoven webs of this invention can be formed into fabrics, garments, clothing, medical garments, surgical gowns, surgical drapes, diapers, training pants, sanitary napkins, panty liners, incontinent wear, bed pads, bags, packaging material, packages, swimwear, body fluid impermeable backsheets, body fluid impermeable layers, body fluid permeable layers, body fluid permeable covers, absorbents, tissues, nonwoven composites, liners, cloth linings, scrubbing pads, face masks, respirators, air filters, vacuum bags, oil and chemical spill sorbents, thermal insulation, first aid dressings, medical wraps, fiberfill, outerwear, bed quilt stuffing, furniture padding, filter media, scrubbing pads, wipe materials, hosiery, automotive seats, upholstered furniture, carpets, carpet backing, filter media, disposable wipes, diaper coverstock, gardening fabric, geomembranes, geotextiles, sacks, housewrap, vapor barriers, breathable clothing, envelops, tamper evident fabrics, protective packaging, and coasters.

In a preferred embodiment the compositions of this invention can be used for disposable diaper and napkin chassis construction, including: baby diaper leg elastic, diaper frontal tape, diaper standing leg cuff, diaper chassis construction, diaper core stabilization, diaper liquid transfer layer, diaper outer cover lamination, diaper elastic cuff lamination, feminine napkin core stabilization, feminine napkin adhesive strip. The diaper may be of various suitable shapes. For example, the diaper may have an overall rectangular shape, T-shape or an approximately hour-glass shape. Other suitable components which may be incorporated in a diaper comprising the compositions described herein include waist flaps and the like which are generally known to those skilled in the art. Examples of diaper configurations suitable for use in connection with the instant invention which may include other components suitable for use on diapers are described in U.S. Pat. No. 4,798,603 to Meyer et al.; U.S. Pat. No. 5,176,668 to Bemardin; U.S. Pat. No. 5,176,672 to Bruemmer et al.; U.S. Pat. No. 5,192,606 to Proxmire et al. and U.S. Pat. No. 5,509,915 to Hanson et al. each of which is hereby incorporated by reference in its entirety.

Preferably, the various components of a diaper comprising the fibers and non-wovens of this invention are assembled together employing various types of suitable attachment means, such as adhesive bonding, ultrasonic bonding, thermal point bonding or combinations thereof. In the shown embodiment, for example, the topsheet and backsheet may be assembled to each other and to the liquid retention structure with lines of adhesive, such as a hot melt, pressure-sensitive adhesive.

In another embodiment, the fibers and or non-wovens of this invention are used in training pants. Various materials and methods for constructing the training pants are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al.; and U.S. Pat. No. 6,645,190 issued Nov. 11, 2003 to Olson et al., which are each incorporated herein by reference in its entirety.

In another embodiment this invention relates to fibers and fabrics comprising:

1. A propylene polymer composition comprising at least 50 mol % propylene, said polymer composition having:
   a) a melt flow rate (MFR, ASTM 1238, 230° C., 2.16 kg) of about 10 dg/min to about 21.5 dg/min;
   b) a dimensionless Stress Ratio/Loss Tangent Index $R_2$ [defined by Eq. (8) below] at 190° C. from about 1.5 to about 28;
   c) an onset temperature of crystallization under flow, $T_{c,rheol}$, (as determined by SAOS rheology, 1° C./min as described below, where said polymer has 0 wt % nucleating agent present), of at least about 131° C.; and
   d) an average meso run length determined by $^{13}$C NMR of at least about 97 or higher; and
   e) optionally, a loss tangent, tan δ, [defined by Eq. (2) below] at an angular frequency of 0.1 rad/s at 190° C. from about 10 to about 70.

2. The propylene polymer composition of paragraph 1 where the composition comprises a combination of two or more propylene polymers.

3. The propylene polymer composition of paragraph 1 or 2 where the propylene polymer composition has a Dimensionless Stress Ratio Index $R_1$ at 190° C. of 1.2 to 4.5.

4. The propylene polymer composition of paragraph 1, 2 or 3 where the propylene polymer composition has a Dimensionless Shear Thinning Index $R_3$ at 190° C. of 6 to 13.

5. The propylene polymer composition of paragraph 1, 2, 3 or 4 where the propylene polymer composition has a Dimensionless Loss Tangent/Elasticity Index $R_4$ at 190° C. of 1.5 to 20.

6. The propylene polymer composition of any of paragraphs 1 to 5 where the propylene polymer composition has a Tmp (second melt, 1° C./min) of 120° C. or more.

7. The propylene polymer composition of any of paragraphs 1 to 6 where the propylene polymer composition has a percent crystallinity of 20 to 80%.

8. The propylene polymer composition of any of paragraphs 1 to 7 where the propylene polymer composition has a glass transition temperature, Tg, of −50° C. to 120° C.

9. The propylene polymer composition of any of paragraphs 1 to 8 where the propylene polymer composition has a crystallization temperature, Tc, (1° C./min) of 15 to 150° C.

10. The propylene polymer composition of any of paragraphs 1 to 9 where the propylene polymer composition has a branching index ($g'_{vis}$) of 0.85 or more.

11. The propylene polymer composition of any of paragraphs 1 to 10 where the propylene polymer composition comprises a propylene polymer having an Mw/Mn of 1 to 7, and/or an Mz/Mw of 1.5 to 2.5.

12. The propylene polymer composition of any of paragraphs 1 to 11 where the propylene polymer composition has a $T_{c,rheol, of}$ 135° C. or more.

13. The propylene polymer composition of any of paragraphs 1 to 12 where the propylene polymer composition has a $T_{mp}$ (10° C. per minute) of 120° C. or more and a $T_{cp}$ (1° C. per minute) of 125° C. or more.

14. The propylene polymer composition of any of paragraphs 1 to 13 where the propylene polymer composition has a supercooling parameter SPC (1° C. per minute) of −11° C. or less and an SPC (10° C. per minute) of −1° C. or less.

15. The propylene polymer composition of any of paragraphs 1 to 14 where the propylene polymer composition has a $T_{mp}$ (1° C. per minute) of 140° C. or more and a dimensionless Stress Ratio Index $R_1$ at 190° C. of 1.2 to 4.6.

16. The propylene polymer composition of any of paragraphs 1 to 15 where the propylene polymer composition has a $T_{cp}$ (1° C. per minute) of 125° C. or more or a $T_{cp}$ (10° C. per minute) of 115° C. or more and a Dimensionless Loss Tangent/Elasticity Index Index $R_4$ at 190° C. of 1.50 to 20.

17. A propylene polymer composition comprising a propylene polymer having:
   1) an MFR in the range from about 10 dg/min to about 21.5 dg/min; AND
   2) a) a Dimensionless Stress Ratio Index $R_1$ [defined by Eq. (7)] at 190° C. from about 1.2 to about 4.5; OR
      b) a Dimensionless Stress Ratio/Loss Tangent Index $R_2$ [defined by Eq. (8)] at 190° C. from about 1.5 to about 28; OR
      c) a Dimensionless Shear Thinning Index $R_3$ [defined by Eq. (9)] at 190° C. from about 6 to about 13; OR
      d) a Dimensionless Loss Tangent/Elasticity Index $R_4$ [defined by Eq. (10)] at 190° C. from about 1.5 to about 20; OR
      e) a Loss Tangent (tan δ) at an angular frequency of 0.1 rad/s [defined by Eq. (2)] at 190° C. from about 14 to about 70; OR
      f) a Stress Ratio (SR) at a shear rate of 500 s$^{-1}$ [defined by Eq. (6)] at 190° C. from about 3.1 to about 6.1; AND
   3) a) An onset temperature of crystallization under flow $T_{c,rheol}$ (via SAOS rheology, 1° C./min) with 0% nucleating agent of at least about 131° C. or higher; OR
      b) a $T_{cp}$ (measured by DSC at a cooling rate of 1° C. per minute) with 0% nucleating agent of at least about 125° C. or higher; OR
      c) a $T_{cp}$ (measured by DSC at a cooling rate of 10° C. per minute) with 0% nucleating agent of at least about 117° C. or higher; OR
      d) a supercooling parameter SCP (measured by DSC at a heating and cooling rate of 10° C./min) with 0% nucleating agent of less than about −2° C.; OR
      e) a supercooling parameter SCP (measured by DSC at a heating and cooling rate of 1° C./min) with 0% nucleating agent of less than about −13° C.; AND
   4) a) an average meso run length determined by $^{13}$C NMR of at least about 97 or higher; OR
      b) a total number of defects (stereo and regio) per 10,000 monomers of less than about 103.

18. The propylene polymer composition of paragraph 17 where the propylene polymer has:
   1) an MFR in the range from about 14 dg/min to about 19 dg/min; AND
   2) a) a Dimensionless Stress Ratio Index $R_1$ [defined by Eq. (7)] at 190° C. from about 2.0 to about 3.0; OR
      b) a Dimensionless Stress Ratio/Loss Tangent Index $R_2$ [defined by Eq. (8)] at 190° C. from about 2.5 to about 6.5; OR
      c) a Dimensionless Shear Thinning Index $R_3$ [defined by Eq. (9)] at 190° C. from about 7.0 to about 10.0; OR
      d) a Dimensionless Loss Tangent/Elasticity Index $R_4$ [defined by Eq. (10)] at 190° C. from about 2.0 to about 6.0; OR e) a Loss Tangent (tan δ) at an angular frequency of 0.1 rad/s [defined by Eq. (2)] at 190° C. from about 35 to about 65; OR f) a Stress Ratio (SR) at a shear rate of 500 s⁻¹ [defined by Eq. (6)] at 190° C. from about 3.3 to about 4.0;

AND 3) a) An onset temperature of crystallization under flow $T_{c,rheol}$ (via SAOS rheology, 1° C./min) with 0% nucleating agent of at least about 134° C. or higher; OR b) a $T_{cp}$ (measured by DSC at a cooling rate of 1° C. per minute) with 0% nucleating agent of at least about 133° C. or higher; OR c) a $T_{cp}$ (measured by DSC at a cooling rate of 10° C. per minute) with 0% nucleating agent of at least about 123° C. or higher; OR d) a supercooling parameter SCP (measured by DSC at a heating and cooling rate of 10° C./min) with 0% nucleating agent of less than about −3.5° C.; OR e) a supercooling parameter SCP (measured by DSC at a heating and cooling rate of 1° C./min) with 0% nucleating agent of less than about −17.0° C.; AND 4) a) an average meso run length determined by ¹³C NMR of at least about 100 or higher; OR b) a total number of defects (stereo and regio) per 10,000 monomers of less than about 100.

19. The composition of any of paragraphs 1 to 18, where propylene polymer is has not been visbroken.

20. The composition of any of paragraphs 1 to 19, where propylene polymer is has been visbroken.

21. The composition of any of paragraphs 1 to 20 having a 1% secant flexural modulus of about 190 kpsi or higher.

22. The composition of any of paragraphs 1 to 21 having a tensile strength at yield of about 4,700 psi or higher.

23. The composition of any of paragraphs 1 to 22 having a heat distortion temperature at 66 psi of about 95° C. or higher.

24. A blend comprising 1) a homopolypropylene having an MFR of 22 dg/min or more (preferably 20 to 30 dg/min, preferably 22 to 28 dg/min, preferably about 25 dg/min) and 2) the composition of any of paragraphs 1 to 23.

25. The blend of paragraph 24 wherein the homopolypropylene having an MFR of 22 dg/min or more is present at 99 wt % to 1 wt %, based upon the weight of the blend (preferably at 95 wt % to 50 wt %, preferably at 95 wt % to 75 wt %) and the composition of any of paragraphs 1 to 22 is present at from 1 wt % to 99 wt %, based upon the weight of the blend, preferably 5 wt % to 50 wt %, preferably 5 wt % to 25 wt %.

26. A diaper comprising the composition or blend of any of paragraphs 1 to 25.

Test Methods

Melt Flow Rate (MFR), defined in gr of polymer per 10 min (g/10 min or its equivalent unit dg/min), was measured according to ASTM D1238 (2.16 kg, 230° C.).

Small angle oscillatory shear (SAOS) frequency sweep melt rheology experiments were performed at 190° C. using a 25 mm cone) (1° and plate configuration on a MCR301 controlled strain/stress rheometer (Anton Paar GmbH). Sample test disks (25 mm diameter, 1 mm thickness) were prepared via compression molding of pellets (which where necessary can be made from fiber samples) at 190° C. using a Schwabenthan laboratory press (200T). Typical cycle for sample preparation is 1 minute without pressure followed by 1.5 minute under pressure (50 bars) and then cooling during 5 minutes between water cooled plates. The sample was first equilibrated at 190° C. for 13 min to erase any prior thermal and crystallization history. An angular frequency sweep was next performed from 500 rad/s to 0.0232 rad/s using 6 points/decade and a strain value of 10% lying in the linear viscoelastic region determined from strain sweep experiments. All experiments were performed in a nitrogen atmosphere to minimize any degradation of the sample during rheological testing.

For purposes of this invention and the claims thereto, the zero-shear-rate viscosity, $\eta_o$, is defined from the frequency dependent storage (G') and loss (G") dynamic moduli and a discrete relaxation spectrum method based on a linear regression (as discussed in Bird, R. B., C. F., Curtiss, R. C. Armstrong, and O. Hassager, *Dynamics of Polymeric Liquids,* 2nd Ed., (Wiley, New York, 1987), Vol. 1. and Doufas, A. K., Rice, L., Thurston, W., "Shear and Extensional Rheology of Polypropylene Melts: Experimental and Modeling Studies", J. Rheology 55, 95-126 (2011)) as follows:

$$\eta_o = \sum_{j=1}^{M} \lambda_j G_j \quad (1)$$

where M is the number of discrete relaxation modes that depends on the range of experimental angular frequencies as outlined in Bird et al. (1987), $\lambda_j$ is a discrete relaxation time of the discrete spectrum and $G_j$ is the corresponding shear modulus.

In case of compositions where the terminal zone (i.e., G' proportional to $\omega^2$ and G" proportional to $\omega$) has not been reached within the frequency range of the experiment thus the complex viscosity $|\eta^*|$ not reaching a plateau value, $\eta_o$ should be measured via melt creep experiments as discussed in Macosko (C. W., *Rheology Principles, Measurements and Applications* (Wiley-VCH, New York, 1994) and Ansari et al. (Ansari, M., S. Hatzikiriakos, A. Sukhadia, D. Rohlfing, "Rheology of Ziegler-Natta and Metallocene High-Density Polyethylenes: Broad Molecular Weight Distribution Effects", Rheol. Acta 50, 17-27, 2011) In all the examples presented in this invention, Eq. (1) for determination of the zero-shear-rate viscosity $\eta_o$ was used. From the storage (G') and loss (G") dynamic moduli [Macosko, C. W., *Rheology Principles, Measurements and Applications* (Wiley-VCH, New York, 1994)], the loss tangent (tan δ) is defined as:

$$\tan\delta = \frac{G''}{G'} \quad (2)$$

The loss tangent, tan δ, especially at low angular frequencies (e.g. 0.1 rad/s), is a measure of melt elasticity and relates to the molecular characteristics (e.g. distribution of short and long chains, density of molecular entanglements, chain branching etc.) of the composition. In the current invention, the first normal stress difference ($N_1$) at a steady shear flow of constant shear rate $\dot{\gamma}$ is determined as a function of the dynamic moduli, G' and G", as follows [Laun, H. M., "Prediction of elastic strains of polymer melts in shear and elongation," J. Rheol. 30 459-501 (1986)]:

$$N_1(\dot{\gamma}) = 2G'\left[1 + \left(\frac{G'}{G''}\right)^2\right]^{0.7} \quad (2)$$

for $$\omega = \dot{\gamma}$$

where G' and G" refer to an angular frequency ω and the temperature of both SAOS and steady shear experiments is identical, N. Eq. (3) is referred to here as "Laun rule". In the present invention, the steady shear stress $\tau_{yx}$ is calculated from the norm of the complex viscosity $|\eta^*|$ according to the Cox-Merz rule [Cox, W. P. and E. H. Merz, "Correlation of dynamic and steady flow viscosities," J. Polym. Sci. 28, 619-621 (1958)]:

$$\tau_{yx}(\dot{\gamma}) = \omega |\eta^*(\omega)| \text{ for } \omega = \dot{\gamma} \qquad (4)$$

where the norm of the complex viscosity is calculated from G' and G" as a function of frequency ω as follows [Macosko, C. W., *Rheology Principles, Measurements and Applications* (Wiley-VCH, New York, 1994)]:

$$|\eta^*(\omega)| = \frac{(G'^2 + G''^2)^{1/2}}{\omega} \qquad (5)$$

The stress ratio (SR) is defined as follows:

$$SR(\dot{\gamma}) = \frac{N_1(\dot{\gamma})}{\tau_{yx}(\dot{\gamma})} \qquad (6)$$

Applicability of both Cox-Merz [Cox and Merz (1957)] and Laun [Laun 1986)] rules was demonstrated for a variety of polypropylene systems in *Shear and Extensional Rheology of Polypropylene Melts: Experimental and Modeling Studies*, Doufas et al., J. Rheol. 55, 95 (2011). Based on the above rheological properties, several rheological indexes are defined related to the molecular characteristics of the composition as follows:
Dimensionless Stress Ratio Index $R_1$:

$$R_1 = (SR(500 \text{ s}^{-1})\eta_o)/2040 \qquad (7)$$

where $\eta_o$ [Eq. (1)] is in units of Pa s.
Dimensionless Stress Ratio/Loss Tangent Index $R_2$:

$$R_2 = \left(\frac{SR(500\text{s}^{-1})\eta_o}{\tan\delta(0.1 \text{ rad/s})}\right)/248 \qquad (8)$$

where $\eta_o$ [Eq. (1)] is in Pa s.
Dimensionless Shear Thinning Index $R_3$ $$R_3 = \frac{\eta_o}{\eta(500\text{s}^{-1})} \qquad (9)$$

where the steady shear viscosity $\eta(500 \text{ s}^{-1})$ is calculated from Eq. (5) and use of the Cox-Merz rule [Cox, W. P. and E. H. Merz, "Correlation of dynamic and steady flow viscosities," J. Polym. Sci. 28, 619-621 (1958)]. *Dimensionless Loss Tangent/Elasticity Index $R_4$*

$$R_4 = \frac{\eta_o}{\tan\delta(0.1 \text{ rad/s})}/8.55 \qquad (10)$$

where $\eta_o$ [Eq. (1)] is in units of Pa s.
As mentioned, the loss tangent, tan δ, at low angular frequency (e.g. 0.1 rad/s) is sensitive to the molecular structure and relates to the melt longest relaxation time as well as creep related properties (e.g. steady state creep compliance and recoverable creep compliance) (C. W. Macosko, *Rheology Principles, Measurements and Applications* (Wiley-VCH, New York, 1994). Therefore, the rheological indexes intrinsic to the composition, e.g. those defined in Equations (7)-(8), (10), can be in principle expressed in terms of the longest relaxation time and melt creep properties.

Crystallization via SAOS rheology: Crystallization was monitored via SAOS rheology, where the sample was cooled down from the molten state (at 190° C.) at a fixed cooling rate using a 25 mm parallel plate configuration on an ARES 2001 (TA Instruments) controlled strain rheometer. Sample test disks (25 mm diameter, 2.5 mm thickness) were made with a Carver Laboratory press at 190° C. Samples were allowed to sit without pressure for approximately 3 minutes in order to melt and then held under pressure for three minutes to compression mold the sample. The disks were originally approximately 2.5 mm thick, however after sample trimming off the parallel plates, a gap of 1.9 mm between the plates was used. Thermal expansion of the tools was taken into account during SAOS testing to maintain a constant gap throughout the test. The sample was first heated from room temperature to 190° C. The sample was equilibrated at 190° C. (molten state) for 15 min to erase any prior thermal and crystallization history. The temperature was controlled reproducibly within ±0.5° C. The sample was then cooled from 190° C. at a constant cooling rate of 1° C./min and an angular frequency of 1 rad/s using a strain of 1% lying in the linear viscoelastic region. For termination of the experiment, a maximum torque criterion was used. Upon the onset of crystallization during the rheological test, the instrument goes into an overload condition when maximum torque is reached and the test is stopped automatically. All experiments were performed in a nitrogen atmosphere to minimize any degradation of the sample during rheological testing. Crystallization was observed by a steep/sudden increase of the complex viscosity and a steep/sudden (step-like) decrease of the loss tangent tan δ (i.e., a plot of complex viscosity vs. temperature and loss tangent vs. temperature depict a neck-like region of sudden change in the rheological properties due to occurrence of crystallization). The "onset crystallization temperature via rheology", $T_{c,rheol}$, is defined as the temperature at which a steep (i.e., neck-like) increase of the complex viscosity and a simultaneous steep decrease of tan δ is observed. The reproducibility of $T_{c,rheol}$ is within ±1° C. The reproducibility of the complex modulus and dynamic moduli as a function of temperature is within 3%.

Differential Scanning Calorimetry (DSC)

Peak crystallization temperature ($T_{cp}$), peak melting temperature ($T_{mp}$) and heat of fusion ($\Delta H_f$) were measured via Differential Scanning calorimetry (DSC) on pellet samples using a DSCQ200 (TA Instruments) unit. The DSC was calibrated for temperature using four standards (tin, indium, cyclohexane and water). The heat flow of indium (28.46 J/g) was used to calibrate the heat flow signal. A sample of 3 to 5 mg of polymer, typically in pellet form, was sealed in a standard aluminum pan with flat lids and loaded into the instrument at room temperature.

In the case of determination of $T_{cp}$ and $T_{mp}$ corresponding to 1° C./min cooling and heating rates, the following procedure was used. The sample was first equilibrated at 25° C. and subsequently heated to 200° C. using a heating rate of 20° C./min (first heat). The sample was held at 200° C. for 5 min to erase any prior thermal and crystallization history. The sample was subsequently cooled down to 95° C. with a constant cooling rate of 1° C./min (first cool). The sample was held isothermal at 95° C. for 5 min before being heated to 200° C. at a constant heating rate of 1° C./min (second heat). The exothermic peak of crystallization (first cool) was analyzed using the TA Universal Analysis software and the peak crystallization temperature ($T_{cp}$) corresponding to 1° C./min cooling rate was determined. The endothermic peak of melting (second heat) was also analyzed using the TA Universal Analysis software and the peak melting temperature ($T_{mp}$) corresponding to 1° C./min cooling rate was determined.

In the case of determination of $T_{cp}$ and $T_{mp}$ corresponding to 10° C./min cooling and heating rates, the following procedure was used. The sample was first equilibrated at 25° C. and subsequently heated to 200° C. using a heating rate of 10° C./min (first heat). The sample was held at 200° C. for 10 min to erase any prior thermal and crystallization history. The sample was subsequently cooled down to 25° C. with a constant cooling rate of 10° C./min (first cool). The sample was held isothermal at 25° C. for 10 min before being heated to 200° C. at a constant heating rate of 10° C./min (second heat). The exothermic peak of crystallization (first cool) was analyzed using the TA Universal Analysis software and the peak crystallization temperature ($T_{cp}$) corresponding to 10° C./min cooling rate was determined. The endothermic peak of melting (second heat) was also analyzed using the TA Universal Analysis software and the peak melting temperature ($T_{mp}$) corresponding to 10° C./min heating rate was determined In either method of determining crystallization and melting peak temperatures, the same cooling and heating rate (1° C./min or 10° C./min) was always kept during the second (cool) and third (heat) cycles, respectively. For example, in cases where $T_{mp}$ is listed with its associated heating rate, it is implied that the cooling rate of the preceding cycle was at the same rate as the heating cycle. The percent crystallinity (X %) is calculated using the formula: [area under the DSC curve (in J/g)/H° (in J/g)]*100, where the area under the DSC curve refers here to the first cool cycle and H° is the heat of fusion for the homopolymer of the major monomner component. These values for H° are to be obtained from the *Polymer Handbook, Fourth Edition*, published by John Wiley and Sons, New York 1999, except that a value of 290 J/g is used as the equilibrium heat of fusion (H°) for 100% crystalline polyethylene, a value of 140 J/g is used as the equilibrium heat of fusion (H°) for 100% crystalline polybutene, and a value of 207 J/g (H°) is used as the heat of fusion for a 100% crystalline polypropylene.

In the present invention, the difference between the melting and crystallization peak temperatures ($T_{mp}-T_{cp}$)) as measured by DSC (either at 1° C./min or 10° C./min temperature ramp rates) is referred to as "the supercooling range" and is expressed in ° C. The "supercooling limit", SCL, is defined according to U.S. Pat. No. 7,807,769 and US 2010/0113718 as follows:

$$SCL = 0.907 T_{mp} - 99.64 \qquad (11)$$

where $T_{mp}$ and SCL are expressed in ° C. U.S. Pat. No. 7,807,769 and US Patent Application Publication No. 2010/0113718 define SCL with $T_{mp}$ corresponding to a heating rate of 10° C./min (second heat), however in the present invention Eq. (11) is also used to define SCL at a heating rate of 1° C./min (second heat). The following parameter referred to as "supercooling parameter" SCP is defined here as follows:

$$SCP = T_{mp} - T_{cp} - SCL \qquad (12)$$

where all parameters on the right hand side of Eq. (12) are expressed in ° C. and refer to either a temperature ramp rate of 1° C./min or 10° C./min as indicated. In Eq. (12), SCL is calculated from Eq. (11).

Molecular Weights (Mw, Mn, Mz and Mv) by Gel-Permeation Chromatography (GPC)

Molecular weight distributions were characterized using Gel-Permeation Chromatography (GPC), also referred to as Size-Exclusion Chromatography (SEC). Molecular weights (weight average molecular weight $M_w$, number average molecular weight $M_n$, Z average molecular weight $M_z$ and viscosity average molecular weight $M_v$) were determined using High-Temperature Gel-Permeation Chromatography equipped with a differential refractive index detector (DRI). Experimental details on the measurement procedure are described in the literature by T. Sun, P. Brant, R. R. Chance and W. W. Graessley, Macromolecules, Volume 34, Number 19, 6812-6820 (2001) and in U.S. Pat. No. 7,807,769.

A Polymer Laboratories PL-GPC-220 high temperature SEC system with triple detection and three Polymer Laboratories PLgel 10 micron Mixed B columns was used. The three detectors in series are: Wyatt DAWN "EOS" MALLS 18 angle laser light scattering detector first, followed by the DRI detector and finally by the Differential Viscometer detector. The detector output signals are collected on Wyatt's ASTRA software and analyzed using a GPC analysis program. The detailed GPC conditions are listed in the Table 8 of U.S. Pat. No. 7,807,769. A theoretical basis for the data analysis can be also found in U.S. Pat. No. 7,807,769.

A nominal flow rate of 0.5 cm³/min, and a nominal injection volume of 300 mL were used. The various transfer lines, columns and differential refractometer (the DRI detector, used mainly to determine elution solution concentrations) are contained in an oven at 145° C.

Standards and samples were prepared in inhibited TCB (1,2,4-trichlorobenzene) solvent. Four NBS polyethylene (PE) standards were used for calibrating the GPC. The PE standards were NIST 1482a, NIST 1483a; NIST1484a (narrow PE standards) and NIST 1475a (broad PE standards). The samples were accurately weighted and diluted to a ~1.5 mg/mL concentration and recorded. The standards and samples were placed on a PL Labs 260 Heater/Shaker at 160° C. for two hours. These were filtered through a 2.0 micron steel filter cup and then analyzed.

The branching index ($g'_{vis}$) is calculated using the output of the SEC-DRI-LS-VIS method (described on page 37 of U.S. Pat. No. 7,807,769 for g') as follows. The average intrinsic viscosity, $[\eta]_{avg}$, of the sample is calculated by:

$$[\eta]_{avg} = \frac{\sum c_i [\eta]_i}{\sum c_i} \qquad (13)$$

where the summations are over the chromatographic slices, i, between the integration limits. The branching index $g'_{vis}$ is defined as:

$$g'_{vis} = \frac{[\eta]_{avg}}{kM_v^\alpha} \qquad (14)$$

where, for purpose of this invention and claims thereto, $\alpha=0.695$ and $k=0.000579$ for linear ethylene polymers, $\alpha=0.705$ and $k=0.0002288$ for linear propylene polymers, and $\alpha=0.695$ and $k=0.000179$ for linear butene polymers. The denominator of Eq. (12) represents the calculated theoretical intrinsic viscosity of a linear polymer. $M_v$ is the viscosity-average molecular weight based on molecular weights determined by LS analysis.

Tacticity Determination by $^{13}$C NMR

Carbon NMR spectroscopy was used to measure meso pentads, stereo and regio defect concentrations in the polypropylene. Carbon NMR spectra were acquired with a 10-mm broadband probe on a Varian spectrometer having a $^{13}$C frequency of at least 100 MHz. The samples were prepared in 1,1,2,2-tetrachloroethane-d2 (TCE). Sample preparation (polymer dissolution) was performed at 140° C. where 0.25 grams of polymer was dissolved in an appropriate amount of solvent to give a final polymer solution of 3 ml. In order to optimize chemical shift resolution, the samples were prepared without chromium acetylacetonate relaxation agent.

Chemical shift assignments for the stereo defects (given as stereo pentads) can be found in the literature [L. Resconi, L. Cavallo, A. Fait, and F. Piemontesi, Chem. Rev. 2000, 100, pages 1253-1345]. The stereo pentads (e.g. mmmm, mmmr, mrm, etc.) can be summed appropriately to give a stereo triad distribution (mm, mr and rr) and the mole percentage diads (m and r). Three types of regio defects were quantified: 2,1-erythro, 2,1-threo and 3,1-insertion. The structures and peak assignments for these are also given in the reference by Resconi et al. The concentrations for all regio defects (punctuations) are given in terms of number of regio defects per 10,000 monomer units ($D_R$). Accordingly, the concentration of stereo defects (punctuations) is given as the number of stereo defects per 10,000 monomer units ($D_S$). The total number of defects per 10,000 monomers ($D_{total}$) is calculated as:

$$D_{total} = D_S + D_R \quad (15)$$

The average meso run length (MRL) represents the total number of propylene units (on the average) between defects (stereo and regio) based on 10,000 propylene monomers and is calculated as follows:

$$MRL = \frac{10{,}000}{D_{total}} \quad (16)$$

The definition of MRL in this invention [Eq. (16)] is based upon the number of structural chain punctuations or defects that result from propylene insertions that have occurred in a non-regular fashion (stereo and regio defects). It does not include the punctuations due to the presence of comonomer (e.g. ethylene in a polypropylene random copolymer). The regio defects each give rise to multiple peaks in the carbon NMR spectrum, and these are all integrated and averaged (to the extent that they are resolved from the other peaks in the spectrum), to improve the measurement accuracy. The chemical shift offsets of the resolvable resonances used in the analysis are tabulated in U.S. Pat. No. 7,807,769. The average integral for each defect is divided by the integral for one of the main propylene signals (CH3, CH, CH2) and multiplied by 10,000 to determine the defect concentration per 10,000 monomers.

Bulk Physical Properties Measurements

The flexural modulus (1% secant flexural modulus) is measured according to ASTM D790A, using a crosshead speed of 1.27 mm/min (0.05 in/min) and a support span of 50.8 mm (2.0 in) using an Instron machine.

The tensile properties such as tensile strength at yield (also referred to here as yield stress) and elongation at yield (also referred to here as yield strain) were measured as per ASTM D638, with a crosshead speed of 50.8 mm/min (2.0 in/min) and a gauge length of 50.8 mm (2.0 in), using an Instron machine.

Heat distortion temperature (HDT) is measured according to ASTM D648 using a load of 0.45 MPa (66 psi) or 1.8 MPa (264 psi) as designated.

POY Fiber Testing

The total denier of the POY fibers expressed in grams per 9000 m of yarn is measured by determining the weight of 90 m of yarn which are winded off the fiber core using an Alfred Suter Co. denier wheel. An average denier per filament (dpf) is defined as the measured denier of the yarn over the number of filaments (72). Excellent agreement was found between the measured dpf and that calculated from the mass throughput per hole and take-up speed as follows:

$$dpf = \frac{9000\, W}{\mu_L} \quad (17)$$

Tensile testing of POY fibers was performed with a Textechno Statimat™ M unit which is a microprocessor based machine that tests the strength and elongation of yarns and fibers. The instrument used was specifically Statimat M, S/N 23523, CRE type equipped with software FPAM 0210E using a Microsoft operating system. For all tests, the gauge length was 100 mm and the stretching speed was 1270 mm/min Nonwoven Fabric Testing Fabric basis weight defined as the mass of fabric per unit area was measured by weighing 3 12"×12" fabric pieces and reporting an average value expressed in g/m$^2$ (gsm).

The fiber thickness is expressed as "denier" or equivalently as "denier per filament" (dpf) and is the weight in grams per 9000 meters of fiber as is commonly known in the art. The fiber diameter and dpf were related in this invention according to the following equation based on the definition and the mass balance of the spinning process:

$$d = \sqrt{\frac{141471\, dpf}{\rho}} \quad (18)$$

where d is the diameter of a single fiber in units of microns and is the fiber density (taken in this invention as 900 kg/m$^3$ for polypropylene).

Fibers were isolated and their diameter (thickness) was measured using the following method: A portion of spun-bonded fibers (taken from the belt before entering the thermal bonding step) was carefully cut from a larger sample using a fresh double-edge razor blade and a small portion of the fiber sample was isolated for thickness measurement. Special care was taken to avoid elongation or deformation of fibers when handling. Fibers were mounted between a slide and coverslip in an immersion fluid and examined using the polarizing light microscope (Olympus BX50) equipped with a rotating stage, crossed polars, 20× objective lens, and digital camera (Optronics) driven by Media Cybernetics ImagePro image processing software. Fibers were examined under the following conditions: 90° crossed polars; condenser aperture fully open (to minimize diffraction effects that increase the apparent thickness of the fibers); fibers rotated to angle of maximum brightness. Digital images of 15 fibers were acquired and calibrated. Fiber diameters were measured to the nearest micrometer using Media Cybernetics ImagePro image processing software. Fiber denier was subsequently calculated from the average measured fiber diameter d via Eq. (18).

Tensile properties of nonwoven fabrics such as tensile strength and % elongation in both machine (MD) and cross (CD) directions were measured according to standard method WSP 110.4 (05) with a gauge length of 200 mm and a testing speed of 100 mm/min, unless otherwise indicated. The width of the fabric specimen was 5 cm. For the tensile testing, an Instron machine was used (Model 5565) equipped with Instron Bluehill 2 (version 2.5) software for the data analysis. From the force-elongation tensile curves, the software reports a tensile modulus value (units N/5 cm/gsm) in both MD and CD directions which is calculated according to the following algorithm:
1. search the data from the first data point to the maximum load value
2. use the first data point and maximum load point as the start and end values respectively.
3. divide the data between the start and end values into 6 equal regions with 0% overlap.
4. apply a least square fit algorithm to all of the points in each region to determine the slope of each region.
5. determine the pair of consecutive regions that has the highest slope sum.
6. from this pair, determine which region has the highest slope and assigns the reported modulus value to that region.

A lower the value of tensile modulus is indicative of a less stiff and softer fabric.

Softness or "hand" as it is known in the art is measured using the Thwing-Albert Instruments Co. Handle-O-Meter (Model 211-10-B/AERGLA). The quality of "hand" is considered to be the combination of resistance due to the surface friction and flexibility of a fabric material. The Handle-O-Meter measures the above two factors using an LVDT (Linear Variable Differential Transformer) to detect the resistance that a blade encounters when forcing a specimen of material into a slot of parallel edges. A 3½ digit digital voltmeter (DVM) indicates the resistance directly in gram force. The "total hand" of a given fabric is defined as the average of 8 readings taken on two fabric specimens (4 readings per specimen). For each test specimen (5 mm slot width), the hand is measured on both sides and both directions (MD and CD) and is recorded in grams. A decrease in "total hand" indicates the improvement of fabric softness.

The Elmendorf tear strength (expressed in gr/gsm) of nonwoven fabrics was measured in both MD and CD directions with an Elmendorf tear machine (Thwing Albert Instrument Company) according to ASTM D 1922.

CD peak elongation (also referred to as CD elongation), and CD peak strength (also referred to as CD strength) are determined according to WSP 110.4 (05), using a gauge length of 200 mm and a testing speed of 100 mm/min MD peak elongation (also referred to as MD elongation), and MD peak strength (also referred to as MD strength) are determined according to WSP 110.4 (05), using a gauge length of 200 mm and a testing speed of 100 mm/min.

Unless otherwise noted, all fabric tests described above were performed at least 20 days from the day of fabric manufacturing to ensure equilibration of properties and account for any effects that may alter the fabric properties over time. Unless otherwise noted, all fabric tests described above were performed at least 20 days from the day of fabric manufacturing to ensure equilibration of properties and account for any effects that may alter the fabric properties over time. Fabric tensile properties measurements herein are unless the contrary is indicated measured using fabrics which have a bonding area of about 18% with about 50 bonding crossing points per cm$^2$. Fabric tensile properties are preferably measured using fabrics that have been calendered at an optimum calendering temperature, defined as a temperature giving the maximum CD tensile strength. Optimum calendering temperatures for the fabrics of the invention are typically in the range of from about 145° C. to about 160° C. Where, as in certain embodiments described hereinafter, calendering is carried out using calender rolls incorporating oil as heating medium, a heating medium temperature will typically need to be selected in order to achieve the desired calendering temperature.

EXAMPLES

A number of controlled rheology propylene polymers were explored, where a base PP resin with MFR of approx. 0.5 to 5 dg/min and preferably from about 0.8 to about 3 dg/min was peroxide cracked (controlled-rheology propylene polymers) in an extruder to obtain a final MFR in the range of 10 to 25 dg/min. It was surprisingly found that resins with a certain range of the key melt rheological, crystallization and tacticity parameters described below exhibited the unexpected combination of excellent spinnability and high fiber/fabric strength even at low basis weight fabrics (e.g. <15 g/m$^2$).

Materials

A propylene polymer PP-1 was treated according to the peroxide visbreaking procedure described below to obtain the compositions of Examples 1 to 8. PP-1 is reactor grade Ziegler-Natta propylene homopolymer in pellet form having a MFR of 2 dg/min, $M_w/M_n$ of about 4.3 and a $T_{mp}$ (10° C./min) of 164.3° C. PP-1 contains an additive package typical of that used in spunmelt nonwoven applications e.g. as disclosed in WO2010/087921.

The composition of Example 9 is an extruder (physical) blend of two propylene polymers: A and B in weight ratio of 60/40. Polymer A with an MFR of about 13 dg/min was obtained in pellet form from peroxide visbreaking treatment of propylene polymer PP-2 according to the procedure described below. PP-2 is a reactor grade Ziegler-Natta propylene homopolymer having a MFR of 4.5 dg/min, $M_w/M_n$ of about 4.7 and a $T_{mp}$ (10° C./min) of about 165° C. Polymer B having an MFR of about 40 dg/min was obtained in pellet form from peroxide visbreaking treatment of propylene polymer PP-3 according to the procedure described below. PP-3 is a reactor grade Ziegler-Natta propylene-ethylene random copolymer of about 2.75% by weight in ethylene with an MFR of about 1.7 dg/min After extruder blending of pelletized polymers A and B in a weight ratio of 60/40, the polymer of example 9 was obtained with an MFR of 23.5 dg/min and an ethylene content of about 1.3% by weight.

Inventive example 20 is a blend of a controlled rheology homo-polypropylene available from ExxonMobil Chemical Company, Houston Tex. under the Tradename PP3155 and propylene polymer PP1 (both in pellet form) in a weight ratio of about 70/30 compounded on a 92 mm twin screw extruder.

Inventive example 21 is a blend of a controlled rheology homo-polypropylene available from ExxonMobil Chemical Company, Houston Tex. under the Tradename PP3155 (MFR of 35 dg/min) and propylene polymer PP1 (both in pellet form) in a weight ratio of 70/30, compounded on a 30 mm twin screw extruder.

Inventive example 22 is a controlled rheology (visbroken) propylene polymer whose base polymer is a blend of a homo-polypropylene available from ExxonMobil Chemical Company, Houston Tex. under the Tradename PP5341E1 (MFR of 0.8 dg/min) and propylene polymer PP1 (both in pellet form) in a weight ratio of 25/75. The base polymer (blend) was treated according to the peroxide visbreaking procedure on a 30 mm twin screw extruder to obtain the inventive compositions of example 22.

Examples 1 to 9 and 21 are Examples illustrating an especially preferred embodiment of the invention. Examples 14 to 20, 22 and 23 herein illustrate a further embodiment of the invention. Reference Examples 10 to 13 relate to polymer compositions outside the scope of the present invention.

Example 23 is a controlled rheology (visbroken) propylene polymer whose polymer is a reactor grade homopolymer polypropylene available from ExxonMobil Chemical Company, Houston Tex. under the Tradename PP5341E1 (MFR of 0.8 dg/min) in pellet form. The base polymer was treated according to the peroxide visbreaking procedure on a 30 mm twin screw extruder to obtain the inventive compositions of example 23.

Reference examples 10-12 relate to Ziegler-Natta controlled-rheology propylene homopolymers having a MFR of 36-39 dg/min and a $T_{mp}$ (10° C./min) of about 163° C. available from ExxonMobil Chemical Company, Houston Tex. under the Tradename PP 3155E3.

Reference example 13 relates to metallocene reactor grade propylene homopolymer having a MFR of 24 dg/min and a $T_{mp}$ (10° C./min) of 152.5° C. available from ExxonMobil Chemical Company, Houston Tex. under the Tradename Achieve™ 3854.

Examples 14 and 15 represent metallocene propylene homopolymer having a melt flow index (230° C., 2.16 kg ISO 1133) of 15 about dg/min and a Tm of about 153° C. available from Total Petrochemicals, Feluy Belgium under the Trade name Lumicene™ MR 2002.

Examples 16 and 17 represent Ziegler-Natta controlled-rheology propylene homopolymer having an MFR of about 18 dg/min and a $T_{mp}$ (10° C./min) of about 165° C. available from Borealis Group, Port Murray N.J. under the Trade name HF420FB.

Example 18 is a Ziegler-Natta controlled rheology propylene homopolymer having an MFR of 13.5 dg/min and a $T_{mp}$ (10° C./min) of 163.7° C. available from Lyondell Basell, Houston, Tex. under the trade name Moplen™ HP552N.

Example 19 is a Ziegler-Natta controlled rheology propylene homopolymer having an MFR of 17 dg/min and a $T_{mp}$ (10° C./min) of 164.7° C. available from Lyondell Basell, Houston, Tex. under the trade name Moplen™ PP567P.

Visbreaking Procedure

The starting propylene polymers were peroxide visbroken (cracked) on a 92 mm twin screw extruder (ZSK 92, Werner Pfleiderer) at a production rate of 3,000 lbs/hr and a screw speed of 440 rpm. A peroxide level of 200 to 500 ppm Lupersol™ 101 (2,5-bis(tert-butylperoxy)-2,5-dimethylhexane) was used to crack the starting polymers (inventive Examples 1-9) to a higher MFR (see table 1). The starting propylene polymers are described under "Materials" above. The extruder had two feeders, one for polymer and one for the peroxide visbreaking agent. The set temperature of the extruder zones and the die was in the range of 190° C. to 220° C., while the melt temperature was in the range of 200° C. to 215° C. depending on the starting propylene polymer and targeted final MFR. A standard 100 mesh wire (150 microns nominal porosity) was used for all extruder runs. In each Example, pellets were produced with a density in the range of 40 to 50 ppg (pellets per gram) using an underwater pelletizer. The pellets can be used to form fibers or fabrics.

The polymer properties of the inventive and reference compositions are reported in Tables 1-7 below:

TABLE 1

List of polymer compositions.

| Example | Reactor (R) or Controlled Rheology (CR) | Final Composition MFR (dg/min) |
|---|---|---|
| 1 | CR | 16.5 |
| 2 | CR | 17.0 |
| 3 | CR | 17.0 |
| 4 | CR | 17.0 |
| 5 | CR | 16.7 |
| 6 | CR | 13.0 |
| 7 | CR | 14.2 |
| 8 | CR | 19.0 |
| 9 | CR | 23.5 |
| 10 | CR | 35.0 |
| 11 | CR | 39.0 |
| 12 | CR | 37.0 |
| 13 | R | 24.0 |
| 14 | R | 15.8 |
| 15 | R | 14.4 |
| 16 | CR | 17.7 |
| 17 | CR | 18.6 |
| 18 | CR | 13.5 |
| 19 | CR | 17.0 |
| 20 | CR (Blend) | 16.7 |
| 21 | CR (Blend) | 15.6 |
| 22 | CR (Blend) | 15.3 |
| 23 | CR | 16.1 |

TABLE 2

Rheological properties of polymer compositions including rheology indexes and onset crystallization temperature under flow determined via SAOS rheology.

| Example | $\eta_o$ (Pa·s) | tanδ@ 0.1 rad/s | SR @ 500 s$^{-1}$ | Rheology Index $R_1$ | Rheology Index $R_2$ | Rheology Index $R_3$ | Rheology Index $R_4$ | $T_{c, rheol}$ (° C.) |
|---|---|---|---|---|---|---|---|---|
| 1 | 1362.1 | 47.1 | 3.68 | 2.5 | 4.3 | 8.2 | 3.4 | 140.0 |
| 2 | 1422.4 | 41.3 | 3.68 | 2.6 | 5.1 | 8.3 | 4.0 | 140.0 |
| 3 | 1293.1 | 56.2 | 3.67 | 2.3 | 3.4 | 8.1 | 2.7 | 137.0 |
| 4 | 1469.8 | 50.1 | 3.74 | 2.7 | 4.4 | 8.3 | 3.4 | 140.0 |
| 5 | 1435.5 | 49.1 | 3.68 | 2.6 | 4.3 | 8.1 | 3.4 | 132.0 |
| 6 | 1737.1 | 34.9 | 3.95 | 3.4 | 7.9 | 9.6 | 5.8 | 138.0 |
| 7 | 1612.1 | 42.3 | 3.86 | 3.0 | 5.9 | 9.1 | 4.5 | 132.0 |
| 8 | 1211.2 | 63.1 | 3.49 | 2.1 | 2.7 | 7.3 | 2.2 | 132.0 |
| 9 | 1090.5 | 45.5 | 3.31 | 1.8 | 3.2 | 7.5 | 2.8 | 136.0 |
| 10 | 702.6 | 82.1 | 2.90 | 1.0 | 1.0 | 5.6 | 1.0 | 128.0 |
| 11 | 706.9 | 71.1 | 2.88 | 1.0 | 1.2 | 5.6 | 1.2 | 130.0 |
| 12 | 694.0 | 87.4 | 2.90 | 1.0 | 0.9 | 5.8 | 0.9 | 136.5 |
| 13 | 952.6 | 161.3 | 3.30 | 1.5 | 0.8 | 5.1 | 0.7 | 124.0 |
| 14 | 1284.5 | 58.2 | 3.63 | 2.3 | 3.2 | 6.9 | 2.6 | 125.0 |

TABLE 2-continued

Rheological properties of polymer compositions including rheology indexes and onset crystallization temperature under flow determined via SAOS rheology.

| Example | $\eta_o$ (Pa·s) | tanδ@ 0.1 rad/s | SR @ 500 s$^{-1}$ | Rheology Index $R_1$ | Rheology Index $R_2$ | Rheology Index $R_3$ | Rheology Index $R_4$ | $T_{c,rheol}$ (°C.) |
|---|---|---|---|---|---|---|---|---|
| 15 | 1404.5 | 63.1 | 4.39 | 3.0 | 3.9 | 6.1 | 2.6 | 124.5 |
| 16 | 1392.2 | 52.6 | 3.54 | 2.4 | 3.8 | 7.7 | 3.1 | 126.0 |
| 17 | 1223.9 | 53.8 | 4.38 | 2.6 | 4.0 | 6.5 | 2.7 | 129.0 |
| 18 | 2319.0 | 12.6 | 4.03 | 4.6 | 29.9 | 14.5 | 21.5 | 130.0 |
| 19 | 1456.9 | 48.9 | 3.70 | 2.6 | 4.4 | 8.3 | 3.5 | 128.5 |
| 20 | 1941.1 | 14.3 | 4.87 | 4.6 | 26.7 | 10.6 | 15.9 | 132.0 |
| 21 | 2041.3 | 14.5 | 4.88 | 4.9 | 27.7 | 11.0 | 16.5 | 137.0 |
| 22 | 1319.5 | 70.1 | 4.97 | 3.2 | 3.8 | 6.7 | 2.2 | 132.0 |
| 23 | 1810.0 | 42.5 | 4.2 | 3.7 | 7.1 | 9.9 | 5.0. | 129.0 |

Figure 2:
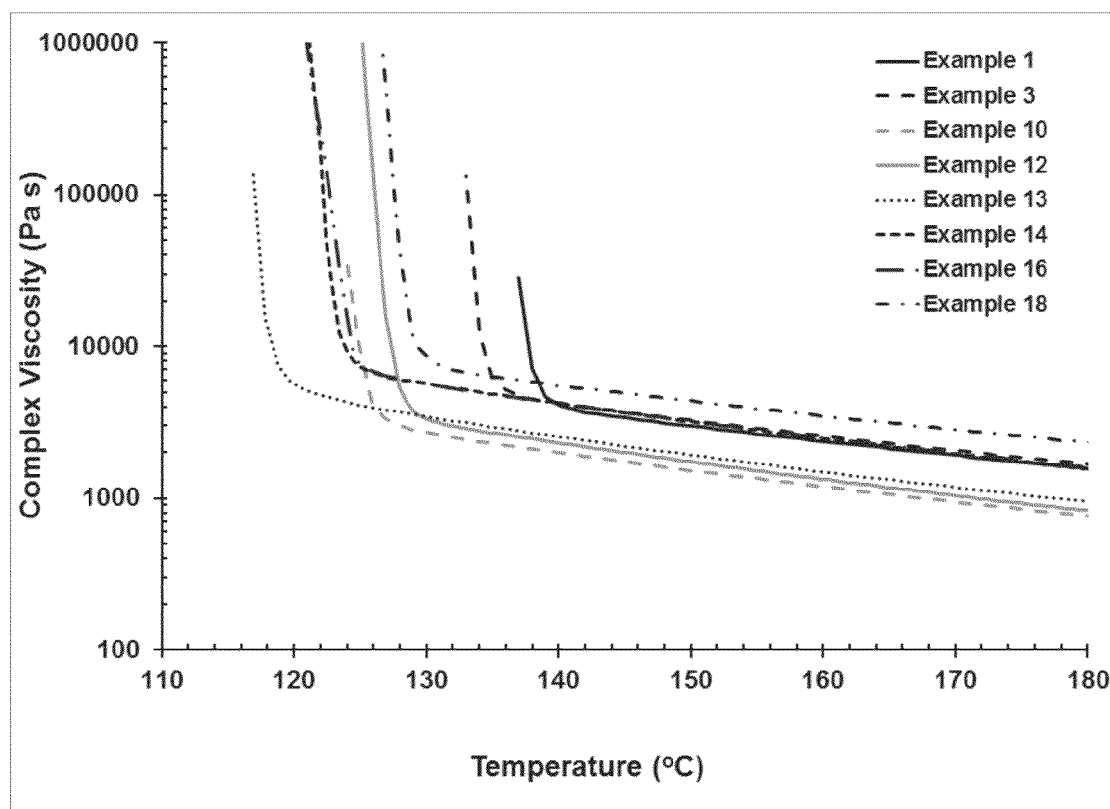
FIG. 2 depicts the complex viscosity of Examples 1, 3, 10, 12, 13, 14, 16, and 18.

FIG. 1 depicts the evolution of the loss tangent (tan δ) under a cooling SAOS rheological experiment according to the "Crystallization via SAOS rheology" method described above. As shown in FIG. 1 and Table 12, the inventive compositions advantageously depict a high crystallization temperature under SAOS rheological conditions (e.g. $T_{c,rheol}$>131° C. and more preferably higher than 135° C.) over all comparative compositions of the prior art. The high value of $T_{c,rheol}$ are hypothesized to lead to faster flow/stress-induced crystallization kinetics under fiber spinning conditions leading to more stable spinnability and favorable crystalline microstructure leading to outstanding balance of fabric mechanical properties as described below. In FIG. 2, the corresponding profiles of the complex viscosity with temperature for certain illustrative compositions are depicted. With decrease of temperature, the complex viscosity increases in a linear function in a log-linear plot. However, below a certain temperature, the complex viscosity abruptly increases due to occurrence of crystallization under SAOS flow.

TABLE 3

Thermal (DSC) properties of polymer compositions at a heating and cooling rate of 1° C./min.

| Example | $T_{c,p}$ (°C.) | $T_{m,p}$ (°C.) | $\Delta H_{cryst}$ (cal/g) | SCL (°C.) | SCP (°C.) |
|---|---|---|---|---|---|
| 1 | 134.7 | 167.7 | 108.2 | 52.5 | −19.5 |
| 2 | 134.4 | 165.1 | 105.2 | 50.1 | −19.4 |
| 3 | 131.4 | 166.8 | 106.5 | 51.6 | −16.3 |
| 4 | 130.1 | 164.7 | 106.4 | 49.7 | −15.1 |
| 5 | 126.0 | 163.8 | 94.2 | 48.9 | −11.1 |
| 6 | 134.4 | 167.7 | 105.0 | 52.4 | −19.2 |
| 7 | 126.3 | 163.1 | 93.6 | 48.3 | −11.5 |
| 8 | 126.2 | 163.5 | 113.0 | 48.7 | −11.3 |
| 9 | 131.6 | 164.6 | 84.8 | 49.7 | −16.7 |
| 10 | 122.3 | 170.2 | 91.1 | 54.7 | −6.8 |
| 11 | 130.7 | 163.4 | 97.1 | 48.5 | −15.9 |
| 12 | 132.6 | 166.7 | 96.3 | 51.5 | −17.5 |
| 13 | 115.9 | 152.5 | 88.7 | 38.7 | −2.0 |
| 14 | 119.2 | 154.0 | 87.6 | 40.0 | −5.3 |
| 15 | 116.0 | 152.7 | 82.6 | 38.9 | −2.1 |
| 16 | 120.7 | 169.1 | 100.8 | 53.7 | −5.3 |
| 17 | 120.5 | 167.4 | 97.6 | 52.2 | −5.3 |
| 18 | 126.8 | 164.7 | 101.9 | 49.8 | −11.9 |
| 19 | 124.7 | 163.5 | 100.3 | 48.7 | −9.9 |
| 20 | 127.5 | 163.9 | 108.1 | 49.0 | −12.6 |
| 21 | 132.51 | 167.1 | 109.6 | 51.9 | −17.3 |
| 22 | 127.89 | 165.1 | 100.4 | 50.1 | −12.9 |
| 23 | 125 | 162.6 | 99.3 | 47.9 | −10.2 |

* The supercooling limit SCL is calculated according to Eq. (11) with $T_{mp}$ at 1° C./min.
* The supercooling parameter SCP is calculated according to Eq. (12) with $T_{mp}$ and $T_{cp}$ at 1° C./min.

TABLE 4

Thermal (DSC) properties of polymer compositions at a heating and cooling rate of 10° C./min.

| Example | $T_{c,p}$ (°C.) | $T_{m,p}$ (°C.) | $\Delta H_{cryst}$ (cal/g) | SCL (°C.) | SCP (°C.) |
|---|---|---|---|---|---|
| 1 | 122.7 | 164.5 | 96.3 | 49.5 | −7.8 |
| 2 | 120.1 | 163.3 | 101.0 | 48.5 | −5.3 |
| 3 | 120.2 | 164.0 | 110.8 | 49.1 | −5.3 |
| 4 | 119.7 | 163.6 | 101.4 | 48.8 | −4.8 |
| 5 | 116.4 | 160.3 | 110.0 | 45.7 | −1.9 |
| 6 | 123.5 | 163.7 | 106.7 | 48.9 | −8.6 |
| 7 | 115.9 | 161.3 | 106.0 | 46.7 | −1.3 |
| 8 | 118.5 | 161.8 | 106.3 | 47.1 | −3.8 |
| 9 | 120.4 | 160.3 | 95.6 | 45.7 | −5.9 |
| 10 | 110.9 | 158.7 | 102.3 | 44.3 | 3.5 |
| 11 | 123.2 | 162.7 | 105.7 | 47.9 | −8.5 |
| 12 | 121.3 | 165.0 | 109.7 | 50.0 | −6.3 |
| 13 | 109.0 | 149.4 | 89.3 | 35.9 | 4.5 |
| 14 | 107.3 | 151.2 | 90.6 | 37.5 | 6.4 |
| 15 | 107.4 | 150.9 | 92.4 | 37.3 | 6.3 |
| 16 | 109.4 | 164.9 | 95.9 | 49.9 | 5.5 |
| 17 | 110.5 | 163.8 | 89.0 | 48.9 | 4.4 |
| 18 | 116.7 | 163.7 | 101.6 | 48.9 | −1.9 |
| 19 | 116.4 | 164.7 | 99.7 | 49.7 | −1.4 |
| 20 | 119.5 | 163.4 | 102.8 | 48.6 | −4.7 |
| 21 | 121.8 | 162.1 | 101.2 | 47.4 | −7.1 |
| 22 | 115.5 | 160.8 | 94.4 | 46.2 | −0.9 |
| 23 | 114.2 | 160.1 | 95.7 | 45.5 | 0.4 |

* The supercooling limit SCL is calculated according to Eq. (11) with $T_{mp}$ at 10° C./min.
* The supercooling parameter SCP is calculated according to Eq. (12) with $T_{mp}$ and $T_{cp}$ at 10° C./min.

TABLE 5

Molecular weight (GPC) and intrinsic viscosity data of polymer compositions.

| Example | $M_w$ (kg/mol) | $M_n$ (kg/mol) | $M_z$ (kg/mol) | $M_v$ (kg/mol) | $M_w/M_n$ | $M_z/M_w$ | Intrinsic Viscosity (dg/l) |
|---|---|---|---|---|---|---|---|
| 1 | 204.9 | 71.7 | 367.1 | 184.8 | 2.86 | 1.79 | 1.249 |
| 2 | 202.9 | 73.8 | 377.8 | 182.7 | 2.75 | 2.12 | 1.194 |
| 3 | 207.1 | 76.1 | 372.6 | 186.9 | 2.72 | 1.80 | 1.198 |
| 4 |  |  |  |  |  |  |  |
| 5 | 203.9 | 65.6 | 376.7 | 183.6 | 3.11 | 1.85 | 1.222 |
| 6 | 205.4 | 71.5 | 360.1 | 185.4 | 2.87 | 1.75 | 1.245 |
| 7 | 209.4 | 61.2 | 382.4 | 187.8 | 3.42 | 1.83 | 1.248 |
| 8 | 190.5 | 58.2 | 344.9 | 171.6 | 3.27 | 1.81 | 1.170 |
| 9 | 190.6 | 56.3 | 395.4 | 168.0 | 3.40 | 2.07 | 1.140 |
| 10 | 183.3 | 62.9 | 358.0 | 164.1 | 2.92 | 1.95 | 1.153 |
| 11 |  |  |  |  |  |  |  |
| 12 | 196.8 | 62.4 | 409.6 | 173.9 | 3.15 | 2.08 | 1.140 |
| 13 | 188.9 | 81.9 | 288.8 | 175.0 | 2.31 | 1.53 | 1.148 |
| 14 | 198.7 | 90.5 | 313.7 | 183.7 | 2.20 | 1.58 | 1.185 |
| 15 | 201.0 | 83.5 | 307.0 | 186.5 | 2.41 | 1.53 | 1.220 |
| 16 | 220.1 | 72.4 | 410.6 | 197.1 | 3.04 | 1.87 | 1.261 |

TABLE 5-continued

Molecular weight (GPC) and intrinsic viscosity data of polymer compositions.

| Example | $M_w$ (kg/ mol) | $M_n$ (kg/ mol) | $M_z$ (kg/ mol) | $M_v$ (kg/ mol) | $M_w/M_n$ | $M_z/M_w$ | Intrinsic Viscosity (dg/l) |
|---|---|---|---|---|---|---|---|
| 17 | 202.5 | 62.2 | 382.3 | 181.1 | 3.26 | 1.89 | 1.212 |
| 18 | 220.9 | 52.3 | 520.9 | 191.0 | 4.23 | 2.36 | 1.239 |
| 19 | 195.8 | 53.6 | 359.2 | 175.4 | 3.65 | 1.84 | 1.161 |
| 20 | 226.6 | 56.3 | 628.4 | 195.5 | 4.02 | 2.77 | 1.315 |
| 21 | 231.7 | 61.1 | 641.1 | 199.3 | 3.79 | 2.77 | 1.330 |
| 22 | 206.8 | 60.4 | 384.5 | 185.1 | 3.43 | 1.86 | 1.238 |
| 23 | 212.5 | 65.7 | 382.0 | 191.2 | 3.24 | 1.80 | 1.276 |

TABLE 6

$^{13}$C NMR tacticity data of polymer compositions

| Example | Average Meso Run Length | % Molar Meso Pentads (mmmm) | Stereo Defects/ 10,000 Propylene Monomers | Regio Defects/ 10,000 Propylene Monomers | Total Defects/ 10,000 Monomers |
|---|---|---|---|---|---|
| 1 | 106.6 | 0.952 | 93 | 1 | 94 |
| 2 | 100.7 | 0.948 | 99 | 0 | 99 |
| 3 | 97.3 | 0.956 | 103 | 0 | 103 |
| 4 | 103.2 | 0.948 | 96 | 1 | 97 |
| 5 | 112.4 | 0.952 | 88 | 1 | 89 |
| 6 | 105.3 | 0.954 | 95 | 0 | 95 |
| 7 | 110.3 | 0.951 | 90 | 1 | 91 |
| 8 | 102.6 | 0.949 | 97 | 1 | 98 |
| 9 | 91.0 | 0.909 | 110 | 0 | 110** |
| 10 | 105.3 | 0.952 | 95 | 0 | 95 |
| 11 | 103.0 | 0.952 | 97 | 0 | 97 |
| 12 | 103.0 | 0.950 | 97 | 0 | 97 |
| 13 | 68.1 | 0.947 | 109 | 35 | 144 |
| 14 | 91.4 | 0.990 | 23 | 85 | 108 |
| 15 | 81.1 | 0.981 | 44 | 79 | 122 |
| 16 | 67.3 | 0.924 | 149 | 0 | 149 |
| 17 | 60.4 | 0.918 | 164 | 2 | 166 |
| 18 | 95.1 | 0.946 | 105 | 0 | 105 |
| 19 | 67.7 | 0.928 | 146 | 2 | 148 |
| 20 | 90.0 | 0.946 | 110 | 2 | 112 |
| 21 | 100.0 | 0.955 | 100 | 0 | 100 |
| 22 | 73.0 | 0.928 | 137 | 0 | 137 |
| 23 | 57.0 | 0.910 | 174 | 0 | 174 |

\* The average meso run length (MSL) is calculated according to Eq. (16).
\*\*Total defects for Example 9 represent the sum of structural chain punctuations or defects (stereo and regio defects) per 10,000 propylene monomers but do not include defects due to the presence of ethylene in this sample.

The above compositions are suitable for forming fibers and nonwoven fabrics. The polymer compositions 1 to 8 and 21 are suitable for making fibers and nonwovens according to a preferred embodiment of this invention. The polymer compositions designated above as Examples 9, 14 to 20, 22 and 23 are suitable for making fibers and nonwovens according to certain other embodiments of the invention. Fibers or fabrics comprising Reference Examples 10 to 13 are included for reference purposes only.

TABLE 7

Bulk Physical properties data of certain illustrative compositions.

| Example | 1% Secant Flexural Modulus (kpsi) | Yield Stress (psi) | % Yield Strain | HDT at 66 psi (° C.) | HDT at 264 psi (° C.) |
|---|---|---|---|---|---|
| 1 | 210 | 5091 | 10.0 | 106.8 | 58.7 |
| 3 | 209 | 5022 | 10.0 | 103.3 | 59.6 |
| 5 | 218 | 5022 | 9.5 | 96.6 | 57.6 |
| 7 | 215 | 5002 | 9.5 | 99.1 | 57.0 |

TABLE 7-continued

Bulk Physical properties data of certain illustrative compositions.

| Example | 1% Secant Flexural Modulus (kpsi) | Yield Stress (psi) | % Yield Strain | HDT at 66 psi (° C.) | HDT at 264 psi (° C.) |
|---|---|---|---|---|---|
| 8 | 219 | 5076 | 9.5 | 99.4 | 58.1 |
| 12 | 213 | 5096 | 9.5 | 106.9 | 60.0 |
| 13 | 192 | 4663 | 9.2 | 98.3 | 56.6 |
| 15 | 199 | 4839 | 9.0 | 99.2 | 57.2 |
| 17 | 187 | 4573 | 11.4 | 88.5 | 53.5 |

The above polymer compositions were then formed into fibers and nonwovens according to the following procedures:

Fiber Spinning (Partially Oriented Yarns)

Fiber spinning experiments were implemented on a Hills pilot line equipped with a Davis Standard 1½ inches extruder and a spinneret of 72 holes each of diameter of 0.60 mm. The polymer pellets were melted and extruded into a metering pump at the desired throughput rate. Melt temperature at the die was kept at 237° C. for all resins for consistency, unless otherwise indicated. The quench air system was kept off Throughput per hole was set at 0.53 gr/min/hole (ghm). Two take-up speeds were explored: 1500 and 3500 m/min as indicated. Under these conditions, fiber denier per filament (dpf) was 3.2 and 1.4 according to Eq. (17) for a take-up speed 1500 m/min and 3500 m/min, respectively. The fiber samples were drawn on a godet roll set at the desired take-up speed and the fibers were collected on a core using a winder. No additional drawing step was performed. Tensile properties of the as-spun fibers are shown in Table 8.

As seen in Table 8, the inventive compositions overall give an excellent balance of fiber tenacity and elongation to break relative to compositions of prior art. For example, inventive composition of example 5 gives significantly higher elongation to break (108%) relative to composition of example 15 (81%) at similar fiber tenacity for both compositions (~3 g/dpf) at a fiber denier of 1.3 dpf. Inventive composition 21 provides unexpectedly very high fiber % elongation (~171%) at high fiber tenacity (~2.9 g/dpf) for 1.3 dpf.

Spinnability was assessed via a "ramp to break" experiment according to which spinning starts at 2000 m/min and is increased at a fixed acceleration rate (480 m/min$^2$) until fiber breakage, while all other processing conditions are kept constant. The speed at which fiber breaks are observed is referred to as max spin speed. Each ramp to break test was performed at a throughput of 0.53 ghm and 0.32 ghm. From the max spin speed and throughput per hole, one can estimate the minimum denier per filament that can be produced for a given resin before breakage according to Eq. (17) above. Excellent spinnability is defined here as the ability of a certain composition to produce fibers of minimum dpf less than about 2.0 and preferably less than about 1.5 at a throughput range of 0.32 to 0.52 ghm. The results of the ramp to break experiments are shown in Table 9.

As depicted in Table 9, the compositions used in Examples 1, 5, 7, 8, 15, 17, 20 and 21, and especially Examples 1, 5, 7, 8 and 21, present excellent spinnability attested by their ability to make thin fibers of less than about 1.5 dpf for a throughput range of 0.32-0.52 ghm.

TABLE 8

Tensile properties (tenacity and elongation at break) of POY fibers for inventive and reference examples.

| Example | Average dpf (0.53 ghm, 1500 m/min) | Tenacity (g/dpf) (0.53 ghm, 1500 m/min) | % Elongation at Break (0.53 ghm, 1500 m/min) | Average dpf (0.53 ghm, 3500 m/min) | Tenacity (g/dpf) (0.53 ghm, 3500 m/min) | % Elongation at Break (0.53 ghm, 3500 m/min) |
|---|---|---|---|---|---|---|
| 1   | 3.1 | 2.8  | 226.8 | 1.2 | 2.95 | 110.0 |
| 5   | 3.1 | 2.69 | 218.6 | 1.3 | 3.00 | 107.9 |
| 7   | 3.1 | 2.67 | 196.1 | 1.4 | 2.49 | 91.1  |
| 8   | 3.1 | 2.66 | 205.2 | 1.3 | 2.93 | 114.9 |
| 12  | 3.0 | 2.63 | 211.4 | 1.3 | 2.94 | 96.5  |
| 13* | 3.0 | 2.98 | 168.3 | 1.3 | 4.11 | 52.0  |
| 15  | 3.0 | 3.04 | 196.2 | 1.3 | 3.18 | 80.6  |
| 17  | 3.0 | 2.83 | 217.9 | 1.4 | 3.00 | 108.2 |
| 21* | 2.9 | 2.01 | 318.7 | 1.3 | 2.87 | 171.4 |

*The melt temperature for Examples 13 and 21 was 265.5° C.

TABLE 9

Maximum (break) spin speed and minimum achievable denier per filament (dpf) for POY fiber spinning for inventive and reference examples

| Example | Max Spin Speed (m/min) at 0.53 ghm | Min dpf at 0.53 ghm | Max Spin Speed (m/min) at 0.32 ghm | Min dpf at 0.32 ghm |
|---|---|---|---|---|
| 1   | 5000 | 0.9 | 4100 | 0.7 |
| 5   | 4300 | 1.1 | 3500 | 0.8 |
| 7   | 3600 | 1.3 | 2500 | 1.2 |
| 8   | 4200 | 1.1 | 3400 | 0.8 |
| 12  | 5000 | 0.9 | 4250 | 0.7 |
| 13* | 4500 | 1.0 | 3500 | 0.8 |
| 15  | 5000 | 0.9 | 4100 | 0.7 |
| 17  | 4900 | 1.0 | 4050 | 0.7 |
| 20  | 3975 | 1.2 | 2825 | 1.0 |
| 21* | 4970 | 0.9 | 2900 | 1.0 |

*The melt temperature for Examples 13 and 21 was 265.5° C.

Spunbond Nonwoven Fabrics

Spunbonded nonwoven fabrics were produced on a Reicofil 4 (R4) line with 3 spunbond (SSS) of about 1.1 m width each having a spinneret of about 6300 holes with a hole (die) diameter of 0.6 mm. For a detailed description of Reicofil spunbonding process, please refer to EP 1340 843 or U.S. Pat. No. 6,918,750. The throughput per hole was about 0.53 ghm. The quench air temperature was 20° C. for all experiments. The ratio of the volume flow VM of process air to the monomer exhaust device to the process air with volume flow V1 escaping from the first upper cooling chamber section into a second lower cooling chamber section (VM/V1) was maintained in the range of from 0.1 to 0.3. Under these conditions, partially oriented filaments of about 1 to 1.4 denier were produced, equivalent to a filament diameter of about 12 to 15 microns [Eq. (18)] above. Line speed was kept constant at 900 m/min. The filaments were deposited continuously on a deposition web with a targeted fabric basis weight for all examples of 10 g/m² (gsm).

The formed fabric was thermally bonded by compressing it through a set of two heated rolls (calenders) for improving fabric integrity and improving fabric mechanical properties. Fundamentals of the fabric thermal bonding process can be found in the review paper by Michielson et al. "Review of Thermally Point-bonded Nonwovens: Materials, Processes, and Properties", J. Applied Polym. Sci. Vol. 99, p. 2489-2496 (2005) or the paper by Bhat et al. "Thermal Bonding of Polypropylene Nonwovens: Effect of Bonding Variables on the Structure and Properties of the Fabrics", J. Applied Polym. Sci., Vol. 92, p. 3593-3600 (2004). The two rolls are referred to as "embossing" and S rolls. In table 10, the set temperature of the two calenders is listed corresponding to the set oil temperature used as the heating medium of the rolls. The calender temperature was measured on both embossing and S rolls using a contact thermocouple and was typically found to be about 10 to 20° C. lower than the set oil temperature. All three spunbonding beams had similar operating conditions. Representative operating conditions are summarized in Table 10, where Air Volume Ratio (V1/V2) is the ratio of the volume flow V1 escaping from the first upper cooling chamber section to the volume flow V2 escaping from the second lower cooling chamber section. In a typical trial, after establishing stable spinning conditions, the calender temperature was varied to create the bonding curve (i.e., tensile strength versus calender temperature). Under the conditions of Table 10, the spinnability of the inventive and comparison compositions was assessed to be excellent.

In Table 11, the fabric tensile properties are summarized corresponding to the calender temperatures resulting in the maximum CD tensile strength. At severe processing conditions of high line speed (900 m/min), high throughput (~0.53 ghm) and low basis weight (10 gsm) that are expected to deteriorate the mechanical properties of the fabrics, most inventive fabrics surprisingly depicted high specific tensile strength in both MD and CD directions (higher than about 2.7 N/5 cm/gsm in MD and higher than about 1.1 N/5 cm/gsm in CD). The inventive fabrics have advantageously lower tensile strength anisotropy (e.g. lower than about 2.6), e.g. 2.9 for the composition of example 15 and 3.2 for reference composition of reference example 13.

In Table 12, it is shown that the fabrics of the present invention lead to advantageously softer fabrics as attested by both a lower tensile modulus (particularly MD modulus) and lower total hand.

Elmendorf tear strength for inventive and reference examples for both MD and CD directions is shown in Table 13. The fabrics of the Examples show overall comparable or higher tear strength as compared with Reference Examples.

TABLE 10

Processing conditions of non-woven spunbonding fabrics of inventive and reference examples. In all cases, 3 spunbonding beams were used (SSS) with a line speed of 900 m/min and a nominal fabric basis weight of 10 g/m².

| Example | Filament Denier | Melt Temperature at the Die (° C.) | Throughput per hole (g/min/hole) | Cabin Pressure (Pa) | Air Volume Ratio $V_1/V_2$ | Calender Set Temperatures For Maximum CD Tensile Strength (° C.) |
|---|---|---|---|---|---|---|
| 1 | 1.3 | 257 | 0.53 | 5300 | 0.12 | 176/165 |
| 4 | 1.2 | 257 | 0.52 | 5300 | 0.12 | 184/165 |
| 5 | 1.3 | 259 | 0.53 | 5300 | 0.13 | 180/165 |
| 9 | 1.1 | 260 | 0.52 | 5000 | 0.15 | 164/160 |
| 10 | 1.2 | 241 | 0.52 | 7000 | 0.11 | 169/165 |
| 11 | N/A | 235 | 0.52 | 5500 | 0.15 | 168/164 |
| 13 | 1.2 | 231 | 0.52 | 7200 | 0.12 | 162/159 |
| 15 | 1.3 | 259 | 0.53 | 5300 | 0.21 | 186/171 |

TABLE 11

Fabric tensile strength properties for inventive and reference examples. The fabric tensile data correspond to fabrics produced at the calender set temperatures of Table 10 resulting in the maximum CD tensile strength. The line speed is 900 m/min.

| Example | Fabric Basis Weight (gsm) | MD Specific Tensile Strength at Peak Load (N/5 cm/gsm) | CD Specific Tensile Strength at Peak Load (N/5 cm/gsm) | Tensile Strength Anisotropy MD/CD | MD % Elongation at Peak Load | CD % Elongation at Peak Load |
|---|---|---|---|---|---|---|
| 1 | 9.5 | 3.19 | 1.22 | 2.61 | 45.8 | 63.3 |
| 4 | 9.8 | 2.68 | 1.14 | 2.35 | 35.1 | 60.4 |
| 5 | 9.7 | 3.01 | 1.16 | 2.58 | 39.5 | 66.4 |
| 9 | 10.2 | 2.55 | 0.96 | 2.65 | 47.8 | 64.5 |
| 10 | 10.7 | 2.39 | 0.97 | 2.46 | 35.1 | 55.7 |
| 11 | 10.0 | 2.76 | 0.93 | 2.97 | 44.2 | 59.0 |
| 13 | 9.8 | 2.73 | 0.85 | 3.23 | 24.3 | 39.0 |
| 15 | 9.9 | 3.35 | 1.14 | 2.93 | 39.0 | 55.3 |

TABLE 12

Fabric stiffness and softness related properties for inventive and reference examples. The listed properties correspond to fabrics produced at the calender set temperatures of Table 10 resulting in the maximum CD tensile strength.

| Example | MD Tensile Modulus (N/5 cm/gsm) | CD Tensile Modulus (N/5 cm/gsm) | MD Hand (gr) | CD Hand (gr) | Total Hand (gr) |
|---|---|---|---|---|---|
| 1 | 29.0 | 2.8 | 8.65 | 3.63 | 6.14 |
| 4 | 26.0 | 2.6 | 9.25 | 4.40 | 6.83 |
| 5 | 32.1 | 2.4 | 8.55 | 3.70 | 6.13 |
| 9 | 23.8 | 1.9 | 7.75 | 3.03 | 5.39 |
| 10 | 23.8 | 2.5 | 8.70 | 3.33 | 6.01 |
| 11 | 28.9 | 2.5 | 9.05 | 3.83 | 6.44 |
| 13 | 37.1 | 3.5 | 10.28 | 3.65 | 6.96 |
| 15 | 36.2 | 2.8 | 9.88 | 3.90 | 6.89 |

TABLE 13

Fabric Elmedorf tear strength for inventive and reference examples. The listed properties correspond to fabrics produced at the calender set temperatures of Table 10 resulting in the maximum CD tensile strength.

| Example | MD Elmendorf Tear Strength (gr/gsm) | CD Elmendorf Tear Strength (gr/gsm) |
|---|---|---|
| 1 | 10.7 | 17.2 |
| 4 | 8.7 | 15.0 |
| 5 | 9.9 | 13.5 |
| 9 | 8.5 | 13.7 |
| 10 | 7.5 | 16.0 |
| 11 | N/A | N/A |
| 13 | 12.8 | 16.5 |
| 15 | 11.5 | 16.7 |

Additional Fabric Properties

Tear properties of fabrics on tongue-shaped test pieces, was determined by DIN EN ISO 13937-4. Nonwoven tear resistance was determined by DIN EN ISO 9073-4. Determination of breaking strength and elongation of nonwoven materials using the grab tensile test was obtained according to DIN EN ISO 9073-18. The bursting strength of fabrics, pneumatic method of determination of bursting strength and bursting distension, was determined according to DIN EN ISO 13938-2. Abrasion resistance of fabrics was determined by the by the Martindale method. Specimen breakdown was determined according to DIN EN ISO 12947-2. Nonwoven bending length was determined by DIN EN ISO 9073-7.

Drapability of nonwovens, including drape coefficient, was determined by DIN EN ISO 9073-9.

Three polymer compositions, a polymer having an MFR of 16.5 made using the same procedure as Example 1 (referred to as EX1-A), Lumicene™ MR2002 and PP3155, were formed into nonwoven fabrics according to the general procedure for Spunbond Nonwoven Fabrics detailed above including that 3 spunbonding beams were used (SSS) with a line speed of 900 m/min and a nominal fabric basis weight of 10 g/m². Specific process conditions are listed in Table A below.

reported in Tables D and E. Achieve™ 3854 is a metallocene propylene homopolymer having a MFR of 24 dg/min available from ExxonMobil Chemical Company, Houston Tex. Lumicene™ MR 2002 is a metallocene propylene homopolymer having a melt flow index (230° C., 2.16 kg ISO 1133) of 15 about dg/min and a Tm of about 153° C. available from Total Petrochemicals, Feluy Belgium. The fabrics were formed by the spunbonded nonwoven fabric process and conditions described above at a nominal fabric basis weight of 10 gsm, except that fabrics produced at a line speed of 300 m/min used one spunbond beam.

TABLE A

Processing conditions of non-woven spunbonding fabrics. In all cases, 3 spunbonding beams were used (SSS) with a line speed of 900 m/min and a nominal fabric basis weight of 10 g/m².

| Example | Resin | Filament Denier (dpf) | Melt Temperature at the Die (° C.) | Throughput per hole (g/min/hol) | Cabin Pressure (Pa) | Air Volume Ratio $V_1/V_2$ | Calender Set Temperatures For Maximum CD Tensile Strength (° C.) |
|---|---|---|---|---|---|---|---|
| A-1 | EX1-A | 1.3 | 258 | 0.53 | 5300 | 0.14 | 180/165 |
| A-2 | Lumicene MR 2002 | 1.3 | 259 | 0.53 | 5300 | 0.21 | 182/171 |
| A-3 | EX1-A | N/A | 245 | 0.53 | 4500 | 0.25 | 168/165 |
| A-4 | Lumicene MR 2002 | 1.4 | 259 | 0.53 | 5300 | 0.21 | 176/171 |
| A-5 | PP3155 | 1.4 | 235 | 0.53 | 5500 | 0.25 | 168/164 |

Grab Tensile data, reported in Table B below were obtained according to the procedure in DIN EN 9073-18. Tongue tear data, reported in Table C, were determined according to DIN EN ISO 9073-4. Burst strength, reported in Table C, were obtained according to ISO 13938-2 1999.

TABLE B

Grab Tensile Properties

| Example | Fabric Basis Weight (gsm) | MD Grab Tensile Peak Load (N) | MD Grab Tensile Peak Load (N/gsm) | MD Length Change at Peak Load (mm) | MD % Elongation at Peak Load | CD Grab Tensile Peak Load (N) | CD Grab Tensile Peak Load (N/gsm) | CD Length Change at Peak Load (mm) | CD % Elongation at Peak Load |
|---|---|---|---|---|---|---|---|---|---|
| A-1 | 9.8 | 40.64 | 4.15 | 35.1 | 46.5 | 21.05 | 2.15 | 58.4 | 76.3 |
| A-2 | 9.8 | 41.53 | 4.24 | 29.8 | 39.5 | 20.7 | 2.11 | 57.8 | 75.6 |
| A-3 | 9.8 | 37.53 | 3.83 | 33.7 | 44.7 | 19.04 | 1.94 | 52.6 | 69.1 |
| A-4 | 9.7 | 42.92 | 4.42 | 32.1 | 42.6 | 21.07 | 2.17 | 50.3 | 66.1 |
| A-5 | 10.4 | 34.65 | 3.33 | 31.7 | 42.1 | 18.24 | 1.75 | 52.1 | 67.9 |

TABLE C

Tongue Tear and Burst Strength

| Example | CD Tear Max Force (N) | MD Tear Max Force (N) | Bursting Strength (kPa) | Burst Height (mm) |
|---|---|---|---|---|
| A-1 | 9.2 | 7.8 | 28.5 | 31.1 |
| A-2 | 9.3 | 8.0 | 21.8 | 28.5 |
| A-3 | 9.4 | 8.8 | 31.0 | 32.5 |
| A-4 | 9.4 | 9.1 | 31.9 | 30.7 |
| A-5 | 7.8 | 5.8 | 26.9 | 31.8 |

A polymer having an MFR of 16.5 made using the same procedure as Example 1 (referred to as EX1-A), Achieve™ 3854, and Lumicene™ MR 2002 were formed into fabrics and then tested for various physical properties. The data are

TABLE D

Fabric tensile properties per WSP 110.4 (05) at low (300 m/min) and high (900 m/min) spunbond line speed conditions.

| Tensile testing conditions: 100 m/min, 200 mm gauge length | Fabric basis weight (gsm) | CD Strength (N/5 cm/gsm) | MD Strength (N/5 cm/gsm) | CD Peak Elongation (%) | MD Peak Elongation (%) |
|---|---|---|---|---|---|
| PP3155 (300 m/min) | 10.1 | 1.27 | 2.35 | 51. | 42.9 |
| PP3155 (900 m/min) | 10.3 | 0.95 | 2.76 | 59.0 | 44.2 |
| Achieve™ 3854 (300 m/min) | 10.0 | 1.32 | 3.14 | 45.5 | 40.4 |
| Achieve™ 3854 (900 m/min) | 9.8 | 0.85 | 2.73 | 39.0 | 24.3 |
| EX1-A (300 m/min) | 10.2 | 1.61 | 2.52 | 56.7 | 45.3 |
| EX1-A (900 m/min) | 9.8 | 1.13 | 2.89 | | 38.4 |

TABLE D-continued

Fabric tensile properties per WSP 110.4 (05) at low (300 m/min) and high (900 m/min) spunbond line speed conditions.

| Tensile testing conditions: 100 m/min, 200 mm gauge length | Fabric basis weight (gsm) | CD Strength (N/5 cm/gsm) | MD Strength (N/5 cm/gsm) | CD Peak Elongation (%) | MD Peak Elongation (%) |
|---|---|---|---|---|---|
| Lumicene ™ MR 2002 (300 m/min) | 10 | 1.70 | 2.92 | 50.3 | 44.6 |
| Lumicene ™ MR 2002 (900 m/min) | 9.8 | 1.21 | 3.33 | | 37.7 |
| US 20110081817 Example 3* | 12.0 | 1.6 | 2.9 | 59 | 65.0 |
| US 20110081817 Example 4* | 12.0 | 1.65 | 3.03 | 66 | 68.0 |
| US 20110081817 Comparative Example 2* | 12.0 | 1.49 | 2.82 | 57 | 56.0 |
| US 20100233927 Example 2* | 12.0 | 1.78 | 3.18 | 69.4 | 66.9 |
| US 20110059668 Example 3* | 12.0 | 1.30 | 2.85 | 66 | 61.0 |

*data taken from cited reference, 300 m/min

TABLE E

Fabric Elmendorf tear strength (ASTM D 1922) at low (300 m/min) and high (900 m/min) spunbond line speed conditions, nominal Fabric basis weight 10 gsm

| speed (m/min) | CD Elmendorf Tear (N/gsm) PP3155 | CD Elmendorf Tear (N/gsm) EX1-A | CD Elmendorf Tear (N/gsm) Lumicene MR 2002 | CD Elmendorf Tear (N/gsm) PP3155 | CD Elmendorf Tear (N/gsm) EX1-A | CD Elmendorf Tear (N/gsm) Lumicene MR 2002 | CD Elmendorf Tear (gr/gsm) Achieve 3854 | MD Elmendorf Tear (gr/gsm) Achieve 3854 |
|---|---|---|---|---|---|---|---|---|
| 300 | 11.8 | 15.9 | 20.5 | 7.8 | 11.0 | 14.7 | 19.4 | 13.1 |
| 900 | 12.7 | 13.1 | 16.1 | 7.0 | 9.6 | 11.6 | 16.5 | 12.8 |

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of" "consisting of", "selected from the group of consisting of", or "is" preceding the recitation of the composition, element, or elements and vice versa.

What is claimed is:

1. A nonwoven fabric comprising polypropylene fibers, wherein said polypropylene fibers comprise a propylene polymer comprising at least 50 mol % propylene, said polymer having:
   a) a melt flow rate (MFR, ASTM 1238, 230° C., 2.16 kg) of about 10 dg/min to about 21.5 dg/min;
   b) a dimensionless Stress Ratio/Loss Tangent Index $R_2$ [defined by Eq. (8) herein] at 190° C. from about 1.5 to about 28;
   c) an onset temperature of crystallization under flow, $T_{c,rheol}$, (as determined by SAOS rheology, 1° C./min as described herein, where said polymer has 0 wt % nucleating agent present), of at least about 131° C.; and
   d) an average meso run length determined by $^{13}C$ NMR of at least about 97 or higher.

2. A nonwoven fabric according to claim 1, wherein said polypropylene fibers are present in an amount of at least 50% by weight, preferably at least 75% by weight, based on the total weight of fibers in said nonwoven fabric.

3. A nonwoven fabric according to claim 1, having a fabric basis weight in the range of 5 to 70 gsm, preferably 7 to 15 gsm.

4. A nonwoven fabric according to claim 1, having a tensile strength anisotropy defined as the ratio of the specific tensile strength in the MD over the specific tensile strength in the CD of less than about 2.7.

5. A nonwoven fabric according to claim 1, having a total hand of less than about 6.8 gr.

6. A nonwoven fabric according to claim 1, having a MD tensile modulus (as defined herein) of less than about 35 N/5 cm/gsm.

7. A nonwoven fabric according to claim 1, having a CD specific tensile strength of at least 1.0 N/5 cm/gsm, a MD specific tensile strength of at least 2.7 N/5 cm/gsm and a total hand of less than about 6.8 gm force or a tensile modulus of less than about 32 N/5 cm/gsm.

8. A nonwoven fabric according to claim 7, having a fabric tensile anisotropy (ratio of MD over CD specific tensile strength as defined herein) of less than about 2.7.

9. A nonwoven fabric according to claim 1, having a CD specific tensile strength of at least 1.1 N/5 cm/gsm, MD specific tensile strength of at least 2.9 N/5 cm/gsm, and total hand of less than about 6.6 gm force or MD tensile modulus of less than about 30 N/5 cm/gsm.

10. A nonwoven fabric according to claim 1, wherein said propylene polymer has:
   a) a melt flow rate (MFR, ASTM 1238, 230° C., 2.16 kg) of about 14 dg/min to about 19 dg/min;
   b) a dimensionless Stress Ratio/Loss Tangent Index $R_2$ [defined by Eq. (8) herein] at 190° C. from about 2.5 to about 6.5;
   c) an onset temperature of crystallization under flow, $T_{c,rheol}$, (as determined by SAOS rheology, 1° C./min as described below, where said polymer has 0 wt % nucleating agent present), of at least about 136° C.; and
   d) an average meso run length determined by $^{13}C$ NMR of from 97 to 140.

11. A nonwoven fabric according to claim 1, wherein the fibers have a dpf value of from 0.3 to 5 dpf.

12. A nonwoven fabric according to claim 1, comprising a plurality of nonwoven layers that are bonded together.

13. A nonwoven fabric according to claim 1, wherein said fibers comprise a propylene polymer composition comprises a combination of two or more propylene polymers.

14. A nonwoven fabric according to claim 1, wherein said nonwoven fabric is a spunbonded nonwoven.

15. A nonwoven fabric according to claim 1, wherein said nonwoven fabric is a meltblown nonwoven.

16. A nonwoven fabric according to claim 1, comprising a laminate comprising a plurality of nonwovens each independently selected from spunbonded nonwovens and meltblown nonwovens.

17. A nonwoven fabric according to claim 1, wherein the propylene polymer composition comprises a propylene polymer having an Mw/Mn of 1 to 7, and/or an Mz/Mw of 1.5 to 2.5.

18. A nonwoven fabric having a fabric basis weight of not more than 15 gsm and comprising polypropylene fibers having a dpf value of 0.3 to 5 dpf, wherein said polypropylene fibers comprise a propylene polymer composition comprising at least 50 mol % propylene, said polymer composition having:
   a) a melt flow rate (MFR, ASTM 1238, 230° C., 2.16 kg) of about 10 to 25 dg/min
   b) a dimensionless Stress Ratio/Loss Tangent Index $R_2$ [defined by Eq. (8)] at 190° C. from 1.5 to 30
   c) an onset temperature of crystallization under flow, $T_{c,rheol}$, (as determined by SAOS rheology, 1° C./min as described below, where said polymer has 0 wt % nucleating agent present), of at least about 123° C. and
   d) an average meso run length determined by $^{13}$C NMR of at least about 55 or higher.

19. A nonwoven fabric according to claim 18, said nonwoven fabric being obtainable by spun-bonding with a production line speed of at least 400 m/min.

20. A nonwoven fabric according to claim 18, wherein said fabric has a fabric tensile anisotropy as defined herein of less than 3.0 when produced at a production line speed of 900 m/min.

21. A nonwoven fabric having a fabric basis weight of not more than 15 gsm and comprising polypropylene fibers having a dpf value of 0.3 to 5 dpf, wherein:
   said nonwoven fabric is obtainable by spun-bonding with a production line speed of at least 400 m/min;
   said polypropylene fibers are composed of a propylene polymer composition comprising at least 50 mol % propylene, said polymer composition having:
   a) a melt flow rate (MFR, ASTM 1238, 230° C., 2.16 kg) of about 10 to 25 dg/min
   b) a dimensionless Stress Ratio/Loss Tangent Index $R_2$ [defined by Eq. (8)] at 190° C. from 1.5 to 30
   c) an onset temperature of crystallization under flow, $T_{c,rheol}$, (as determined by SAOS rheology, 1° C./min as described below, where said polymer has 0 wt % nucleating agent present), of at least about 123° C. and
   d) an average meso run length determined by $^{13}$C NMR of at least about 55 or higher; and
   said fabric has a ratio of CD elongation to CD peak Strength of 40 or more (when measured at speed of 200 mm/min, 100 mm gauge length) and a CD strength of 1.0 N/5 cm/gsm or more (when measured at speed of 100 mm/min, 200 mm gauge length).

22. A nonwoven fabric according to claim 21 having a CD strength of Y N/5 cm/gsm or more, where Y=−0.0005(X)+ 1.41 (preferably 1.45, preferably 1.5, preferably 1.6), where X is the production line speed of fabric and is at least 400 m/min.

23. A nonwoven fabric according to claim 21, obtainable by spunbonding with a line speed of at least 600 m/min.

24. A laminate fabric comprising a nonwoven fabric according to claim 21 and at least one further fabric layer.

25. A polypropylene fiber comprising a propylene polymer comprising at least 50 mol % propylene, said polymer having:
   a) a melt flow rate (MFR, ASTM 1238, 230° C., 2.16 kg) of about 10 dg/min to about 21.5 dg/min;
   b) a dimensionless Stress Ratio/Loss Tangent Index $R_2$ [defined by Eq. (8) herein] at 190° C. from about 1.5 to about 28;
   c) an onset temperature of crystallization under flow, $T_{c,rheol}$, (as determined by SAOS rheology, 1° C./min as described herein, where said polymer has 0 wt % nucleating agent present), of at least about 131° C.; and
   d) an average meso run length determined by $^{13}$C NMR of at least about 97 or higher.

26. A fiber according to claim 25, having a dpf value of from 0.3 to 5 dpf.

27. A fiber according to claim 25, wherein the fiber is a yarn comprising a plurality of polypropylene filaments having a dpf value of from 0.3 to 5 dpf.

28. A fiber according to claim 25, wherein the fiber is a monofilament of 0.3 to 5 denier.

29. Staple fiber comprising a multiplicity of fibers according to claim 25.

30. An article comprising a multiplicity of fibers according to claim 25.

31. An article comprising a one or more nonwoven fabrics according to claim 1.

32. A diaper comprising one or more nonwoven fabrics according to claim 1.

* * * * *